United States Patent
Yi et al.

(10) Patent No.: US 11,529,370 B2
(45) Date of Patent: *Dec. 20, 2022

(54) USE OF COMPOSITION COMPRISING STEM CELL-DERIVED EXOSOME AS EFFECTIVE INGREDIENT IN STRENGTHENING SKIN BARRIER AND IMPROVING SKIN BARRIER FUNCTION

(71) Applicant: ExoCoBio Inc., Seoul (KR)

(72) Inventors: Yong Weon Yi, Seoul (KR); Byong Seung Cho, Gunpo-si (KR)

(73) Assignee: ExoCoBio Inc., Seoul (KR)

( * ) Notice: Subject to any disclaimer, the term of this patent is extended or adjusted under 35 U.S.C. 154(b) by 351 days.

This patent is subject to a terminal disclaimer.

(21) Appl. No.: 16/878,850

(22) Filed: May 20, 2020

(65) Prior Publication Data
US 2020/0276233 A1 Sep. 3, 2020

Related U.S. Application Data

(63) Continuation of application No. PCT/KR2018/013751, filed on Nov. 13, 2018.

(30) Foreign Application Priority Data

| Nov. 24, 2017 | (KR) | 10-2017-0158950 |
| Jun. 22, 2018 | (KR) | 10-2018-0071805 |
| Aug. 10, 2018 | (KR) | 10-2018-0093873 |

(51) Int. Cl.

| A61K 35/12 | (2015.01) |
| A61K 8/02 | (2006.01) |
| A61K 8/98 | (2006.01) |
| A61K 9/00 | (2006.01) |
| A61K 9/06 | (2006.01) |
| A61Q 19/00 | (2006.01) |

(52) U.S. Cl.
CPC ............ *A61K 35/12* (2013.01); *A61K 8/0212* (2013.01); *A61K 8/0216* (2013.01); *A61K 8/98* (2013.01); *A61K 9/0019* (2013.01); *A61K 9/06* (2013.01); *A61K 2800/884* (2013.01); *A61Q 19/00* (2013.01)

(58) Field of Classification Search
CPC .... A61K 35/12; A61K 8/0212; A61K 8/0216; A61K 8/98; A61K 9/0019; A61K 9/06; A61K 2800/884; A61Q 19/00
See application file for complete search history.

(56) References Cited

U.S. PATENT DOCUMENTS

| 10,071,050 B2 * | 9/2018 | Cho | A61K 35/28 |
| 2012/0107413 A1 * | 5/2012 | Lim | A61P 9/10 |
| | | | 435/317.1 |
| 2014/0031256 A1 | 1/2014 | Lim | |
| 2015/0125950 A1 * | 5/2015 | Lim | C12N 5/0668 |
| | | | 435/325 |
| 2017/0165194 A1 * | 6/2017 | Meng | A61Q 19/00 |

FOREIGN PATENT DOCUMENTS

| CN | 107158035 A | 9/2017 |
| EP | 3639832 A2 | 4/2020 |
| JP | 2003-192525 A | 7/2003 |
| JP | 2014-218481 A | 11/2014 |
| JP | 2015-230222 A | 12/2015 |
| JP | 2016-60718 A | 4/2016 |
| KR | 10-2017-0044999 A | 4/2017 |
| WO | 2015/009325 A1 | 1/2015 |
| WO | 2016/072821 A1 | 5/2016 |
| WO | 2017/023690 A1 | 2/2017 |

OTHER PUBLICATIONS

Kim et al., Significance of Skin Barrier Dysfunction in Atopic Dermatitis. Allergy Asthma Immunol Res. May 2018;10(3):207-215. (Year: 2018).*
Yoon-Jin Kim et al., "Exosomes derived from human umbilical cord blood mesenchymal stem cells stimulates rejuvenation of human skin", Biochemical and Biophysical Research Communications, 2017, vol. 493, pp. 1102-1108 (7 Pages).
Amy S. Paller et al., "Therapeutic pipeline for atopic dermatitis: End of the drought?" J. Allergy Clin. Immunol., 2017, vol. 140 , No. 3, pp. 633-643 (11 pages total).
International search report for PCT/KR2018/013751 dated Apr. 16, 2019.
Written Opinion for PCT/KR2018/013751 dated Apr. 16, 2019.
Written Opinion for PCT/KR2018/013751 dated Jan. 10, 2020.

* cited by examiner

*Primary Examiner* — Robert A Wax
*Assistant Examiner* — Olga V. Tcherkasskaya
(74) *Attorney, Agent, or Firm* — Sughrue Mion, PLLC

(57) ABSTRACT

A composition for strengthening skin barrier or improving skin barrier function is able to improve objective indicators related to the protection of skin barrier, the strengthening of skin barrier, and/or the improvement of skin barrier function. The composition exhibits the effects of increasing the amount of ceramides, dihydroceramides and sphingoid bases, increasing the activities of enzymes that are involved in the synthesis thereof, and decreasing the activities of enzymes that are involved in the degradation thereof. In addition, the composition is able to restore skin barrier function by reducing TSLP, IL-4, and IL-13 which are closely associated with skin barrier damage, and thus interrupting a vicious circle in which the lipids and proteins contributing to skin barrier decrease.

24 Claims, 39 Drawing Sheets
(2 of 39 Drawing Sheet(s) Filed in Color)
Specification includes a Sequence Listing.

FIG. 1C
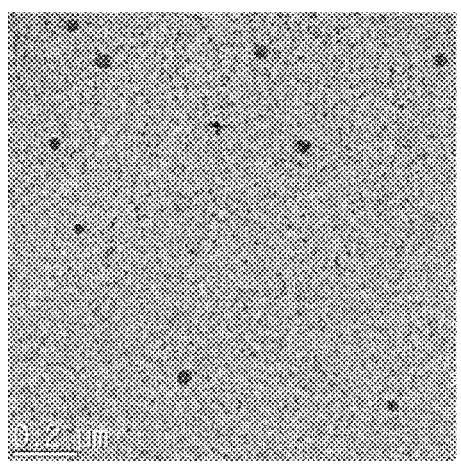
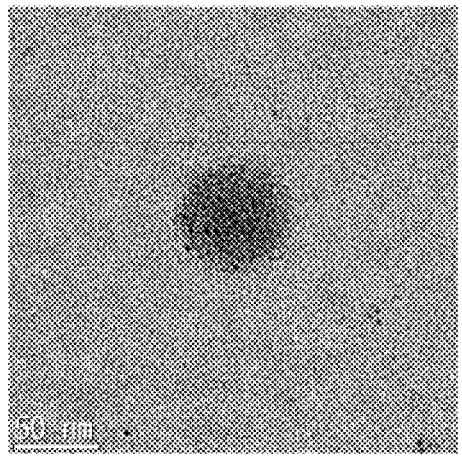

FIG. 1E
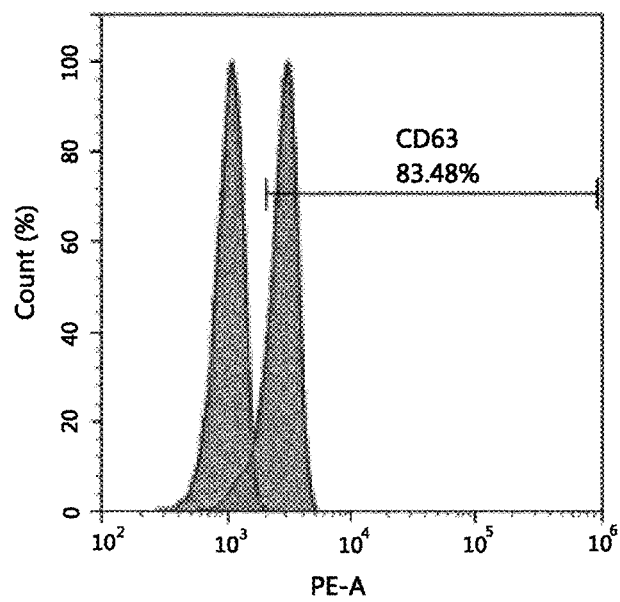
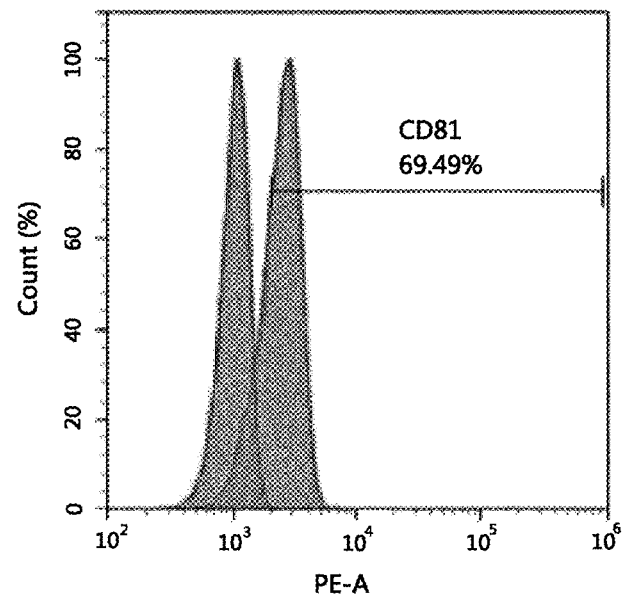

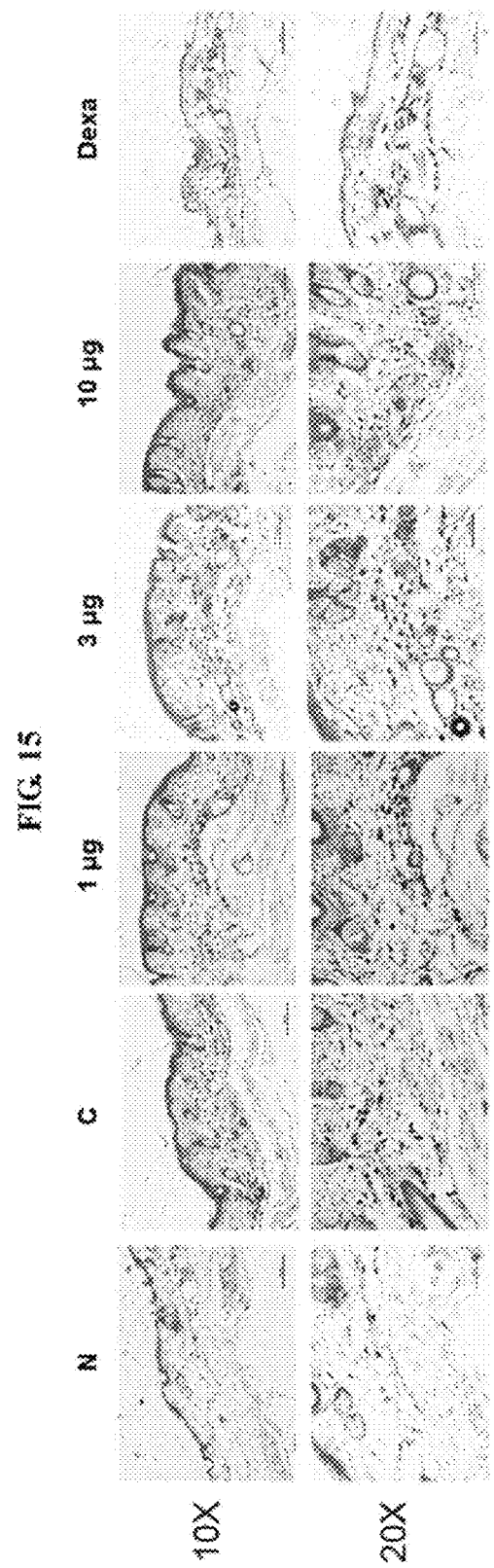

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: TNF-alpha forward primer

<400> SEQUENCE: 1
tctcatcagt tctatggccc agac                                            24

<210> SEQ ID NO 2
<211> LENGTH: 24
<212> TYPE: DNA
<213> ORGANISM: Artificial Sequence
<220> FEATURE:
<223> OTHER INFORMATION: TNF-alpha reverse primer

<400> SEQUENCE: 2
ggcaccacta gttggttgtc tttg                                            24

<210> SEQ ID NO 3
<211> LENGTH: 24
<212> TYPE: DNA
<213> ORGANISM: Artificial Sequence
<220> FEATURE:
<223> OTHER INFORMATION: iNOS forward primer

<400> SEQUENCE: 3
gctaccacat tgaagaagct ggtg                                            24

<210> SEQ ID NO 4
<211> LENGTH: 24
<212> TYPE: DNA
<213> ORGANISM: Artificial Sequence
<220> FEATURE:
<223> OTHER INFORMATION: iNOS reverse primer

<400> SEQUENCE: 4
ccataggaaa agactgcacc gaag                                            24

<210> SEQ ID NO 5
<211> LENGTH: 24
<212> TYPE: DNA
<213> ORGANISM: Artificial Sequence
<220> FEATURE:
<223> OTHER INFORMATION: GAPDH forward primer
```

```
<400> SEQUENCE: 5
gacatcaaga aggtggtgaa gcag                                          24

<210> SEQ ID NO 6
<211> LENGTH: 24
<212> TYPE: DNA
<213> ORGANISM: Artificial Sequence
<220> FEATURE:
<223> OTHER INFORMATION: GAPDH reverse primer

<400> SEQUENCE: 6
ccctgttgct gtagccgtat tcat                                          24

<210> SEQ ID NO 7
<211> LENGTH: 24
<212> TYPE: DNA
<213> ORGANISM: Artificial Sequence
<220> FEATURE:
<223> OTHER INFORMATION: IL-6 forward primer

<400> SEQUENCE: 7
gccagagtcc ttcagagaga taca                                          24

<210> SEQ ID NO 8
<211> LENGTH: 24
<212> TYPE: DNA
<213> ORGANISM: Artificial Sequence
<220> FEATURE:
<223> OTHER INFORMATION: IL-6 reverse primer

<400> SEQUENCE: 8
attggatggt cttggtcctt agcc                                          24

<210> SEQ ID NO 9
<211> LENGTH: 24
<212> TYPE: DNA
<213> ORGANISM: Artificial Sequence
<220> FEATURE:
<223> OTHER INFORMATION: IL-1beta forward primer

<400> SEQUENCE: 9
gcaacgacaa aatacctgtg gcct                                          24

<210> SEQ ID NO 10
<211> LENGTH: 24
<212> TYPE: DNA
<213> ORGANISM: Artificial Sequence
<220> FEATURE:
<223> OTHER INFORMATION: IL-1beta reverse primer

<400> SEQUENCE: 10
agttggggaa ctctgcagac tcaa                                          24
```

USE OF COMPOSITION COMPRISING STEM CELL-DERIVED EXOSOME AS EFFECTIVE INGREDIENT IN STRENGTHENING SKIN BARRIER AND IMPROVING SKIN BARRIER FUNCTION

CROSS REFERENCE

This application is a Bypass Continuation of International Application No. PCT/KR2018/013751 filed Nov. 13, 2018, claiming priority based on Korean Patent Application No. 10-2017-0158950 filed Nov. 24, 2017, Korean Patent Application No. 10-2018-0071805 filed Jun. 22, 2018 and Korean Patent Application No. 10-2018-0093873 filed Aug. 10, 2018, the entire contents of which are incorporated herein by reference.

TECHNICAL FIELD

The present invention relates to the use of a composition containing stem cell-derived exosomes as an active ingredient in strengthening skin barrier or improving skin barrier function.

Moreover, the present invention relates to a pharmaceutical composition, skin external preparation and cosmetic composition including the above composition for strengthening skin barrier or improving skin barrier function.

BACKGROUND ART

The skin is generally composed of three layers: epidermis, dermis and subcutaneous fat tissue. The epidermis is divided into *stratum corneum, stratum lucidum, stratum granulosum* and *stratum basale*, from the outside to the inside. The *stratum corneum*, which is the outermost layer of the epidermis, is a structure playing the most important role in skin barrier function, and is composed of anucleated flat corneocytes and *stratum corneum* (SC) intercellular lipids. Between the corneocytes of the *stratum corneum*, various types of lipids are present, such as sphingolipids, phospholipids, cholesterol sulfate, neutral lipids and the like. These lipids present between the corneocytes function as a skin barrier that prevents the evaporation of skin moisture and protects the skin from external irritants or contaminants.

In particular, a multi-lamellar lipid layer or multi-lamellar structure formed of intercellular lipids, such as ceramides, cholesterols and fatty acids, which are synthesized by the corneocytes, functions as a skin barrier that prevents excessive loss of skin moisture and protects the skin from external allergens or harmful substances which may penetrate into the skin. Ceramides are N-acylated sphingoid compounds in which fatty acids are amide-bonded to sphingoid bases such as sphingosine, phytosphingosine, or sphinganine. In addition, it is known that the corneocyte envelope is composed of envelope proteins such as involucrin, loricrin and filaggrin, and among ceramides, hydroxyceramides strongly bind to these proteins and strengthen the skin barrier structure. Thus, ceramides and hydroxyceramides contribute to forming the skin barrier of the multi-lamellar lipid layer and strengthening the protein skin barrier structure, respectively. Accordingly, it is considered that the increased production of ceramides, hydroxyceramides and/or sphingoid bases, the increased activities of enzymes which are involved in the synthesis thereof, and the decreased activities of enzymes which are involved in the degradation thereof, contribute to strengthening the skin barrier.

Meanwhile, the skin barrier may be damaged due to various causes, such as skin stress caused by various stresses or environmental pollution, frequent face washing, natural skin aging, and loss-of-function mutations in filaggrin gene (FLG). When the skin barrier is damaged, chemicals and microorganisms can easily penetrate into the skin and cause dermatitis, dry skin, and the like.

Therefore, in order to preemptively protect, strengthen or improve the skin barrier before damage to the skin barrier occurs, compositions or functional cosmetics for strengthening the skin barrier or moisturizing the skin have recently attracted attention. For example, a humectant having the property of absorbing moisture or an occlusive moisturizer that prevents moisture evaporation is used to enhance the skin barrier or improve skin barrier function. Once the skin barrier is damaged, the damaged skin barrier is not easily repaired even when a moisturizer is applied, and hence steroid drugs are prescribed. However, the long-term use of the steroid drugs may cause skin atrophy or blood capillary enlargement, and may rather weaken skin barrier function. Therefore, it is important to protect or strengthen the skin barrier or improve skin barrier function before the skin barrier is damaged.

In view of these problems, studies on the strengthening of the skin barrier or the improvement of skin barrier function based on natural substances have been actively conducted. In the case of compositions for strengthening the skin barrier or improving skin barrier function based on these natural substances, the amount of an active ingredient in the natural extract is low, and hence a large amount of the natural extract needs to be used to obtain the effect of strengthening the skin barrier or improving skin barrier function. In the majority of cases, the fact that these compositions are based on natural substances has been emphasized in marketing, but there is a need for more scientific research on the practical efficacies of natural substances on the strengthening of the skin barrier or the improvement of skin barrier function.

Meanwhile, methods for ameliorating or treating skin conditions or diseases using stem cells have been proposed. Embryonic stem cells or fetal tissue-derived stem cells have an excellent ability to differentiate and excellent regeneration and treatment abilities, and cause less rejection, but these stem cells are not clinically applicable due to ethical issues and potential risk of tumor formation. As an alternative thereto, methods for ameliorating or treating skin conditions or diseases using adult stem cells have been proposed. However, the use of allogeneic adult stem cells, not patient's autologous adult stem cells, may pose a risk of causing graft-versus-host disease. When autologous adult stem cells are used for treatment, a problem arises that a process of culturing adult stem cells isolated from a patient is necessary, which is complicated and costly.

In recent years, in view of the above-described problems of stem cells, attempts have been made to ameliorate or treat skin conditions or diseases using conditioned media obtained by culturing adult stem cells. However, the conditioned media of adult stem cells contain not only various proteins, cytokines, and growth factors secreted by adult stem cells, but also components such as waste products secreted during growth of the cells, antibiotics added to prevent contamination, animal-derived serum and the like. Thus, when the conditioned media are used on the skin, the skin is highly likely to be exposed to various risks.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells shed various membraneous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

However, although various studies have been conducted which suggest a possibility for the treatment of some diseases using exosomes, more detailed clinical and non-clinical studies are required, and in particular, there is a need to develop a technology using exosomes, which can be applied for the treatment of a variety of diseases, by scientifically identifying a variety of targets on which exosomes act.

The present inventors have made efforts to develop a novel material which has a better effect of strengthening the skin barrier or improving skin barrier function and is safer than conventional moisturizers or steroid drugs known with respect to the strengthening of the skin barrier or the improvement of skin barrier function. Accordingly, the present inventors have conducted extensive studies on the novel use of exosomes derived from stem cells, and as a result, have found that exosomes isolated from the conditioned media of stem cells can solve the safety problems of the stem cells themselves or the conditioned media as described above, and is effective for strengthening the skin barrier or improving skin barrier function, thereby completing the present invention.

Meanwhile, it is to be understood that the matters described as the background art are intended merely to aid in the understanding of the background of the present invention and are not admitted as prior art against the present invention.

SUMMARY OF INVENTION

It is an object of the present invention to provide the use of a composition comprising stem cell-derived exosomes as an active ingredient in strengthening skin barrier or improving skin barrier function.

Another object of the present invention is to provide a pharmaceutical composition, skin external composition and cosmetic composition including the above composition for strengthening skin barrier or improving skin barrier function.

Still another object of the present invention is to provide a cosmetic method for regulating mammalian skin conditions, except for treatment purposes, by strengthening skin barrier or improving skin barrier function using the above composition.

Yet another object of the present invention is to provide a method for preventing, suppressing, alleviating, ameliorating or treating a skin disease caused by impaired skin barrier function using the above composition.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

To achieve the above objects, the present invention provides a composition for strengthening skin barrier or improving skin barrier function comprising stem cell-derived exosomes as an active ingredient.

As used herein, the term "exosomes" refers to vesicles of tens to hundreds of nanometers in size (preferably, about 30 to 200 nm), which consist of a phospholipid bilayer membrane having the same structure as that of the cell membrane (however, the particle size of exosomes is variable depending on the type of cell from which the exosomes are isolated, an isolation method and a measurement method) (Vasiliy S. Chernyshev et al., "Size and shape characterization of hydrated and desiccated exosomes", Anal Bioanal Chem, (2015) DOI 10.1007/s00216-015-8535-3). These exosomes contain proteins, nucleic acids (mRNA, miRNA, etc.) and the like which are called exosome cargo. It is known that exosomes' cargo includes a wide range of signaling factors, and these signaling factors are specific for cell types and regulated differently depending on secretory cells' environment. It is known that exosomes are intercellular signaling mediators secreted by cells, and various cellular signals transmitted through them regulate cellular behaviors, including the activation, growth, migration, differentiation, dedifferentiation, apoptosis, and necrosis of target cells.

Meanwhile, the term "exosomes" as used herein is intended to include all vesicles (e.g., exosome-like vesicles) which are secreted from stem cells and released into extracellular spaces, and have a nano-sized vesicle structure and a composition similar to that of exosomes. The type of stem cells is not particularly limited, but the stem cells may preferably be mesenchymal stem cells, for example, stem cells derived from adipose, bone marrow, umbilical cords or umbilical cord blood, more preferably adipose-derived stem cells. The adipose-derived stem cells are not particularly limited as long as they do not pose a risk of infection with a pathogen and do not cause immune rejection, but they are preferably human adipose-derived stem cells.

However, as exosomes used in the present invention, various exosomes that are being used in the art or may be used in the future may, of course, be used as long as they are effective in strengthening skin barrier or improving skin barrier function, and do not cause adverse effects on the human body. Therefore, it should be noted that exosomes isolated according to the isolation method of Examples described below should be understood as an example of exosomes that may be used in the present invention, and the present invention is not limited thereto.

As used herein, the expression "strengthening skin barrier or improving skin barrier function" means protecting the skin barrier of the *stratum corneum*, strengthening the skin barrier of the *stratum corneum*, or improving the skin barrier function of the *stratum corneum*, and does not mean regenerating dermis or subcutaneous fat tissue or improving the function thereof. For example, the expression "strengthening skin barrier or improving skin barrier function" means resulting in the protection of the skin barrier of the *stratum corneum*, the strengthening of the skin barrier of the *stratum corneum*, and/or the improvement of the skin barrier function of the *stratum corneum*, in a true sense, by improving skin barrier indicators such as improved production of ceramides, dihydroceramides and/or sphingoid bases, preventing the loss of moisture in the *stratum corneum*, improving the indicator of loss of moisture in the *stratum corneum*, for example, transepidermal water loss (TEWL), increasing skin hydration, and the like.

As used herein, the term "skin moisturizing" means appropriately controlling the loss of moisture from the skin (moisture evaporation) and the like, and maintaining in vivo homeostasis. The term "skin trouble" refers to a skin condition in which the skin turns red and itchy due to external stimulation or physical changes, and in severe cases, small bumps or pimples occur.

The limited effects of stem cell-derived exosomes on wrinkle amelioration and skin regeneration were reported. However, skin regeneration using exosomes in the conventional art is not directed to the protection of the skin barrier of the *stratum corneum*, the strengthening of the skin barrier of the *stratum corneum*, or the improvement of the skin barrier function of the *stratum corneum*, but is directed to ameliorating wrinkles or restoring skin elasticity by regenerating subcutaneous fat tissue. In addition, there have been attempts to use stem cells, stem cell conditioned media and the like to heal wounds by regenerating the dermal layer of the skin, and to improve skin elasticity by regenerating subcutaneous fat tissue. However, it is not yet known that the use of exosomes isolated and purified from the conditioned media of stem cells is effective for "strengthening skin barrier or improving skin barrier function" as defined above.

When the composition for strengthening skin barrier or improving skin barrier function according to the present invention is used as a pharmaceutical composition, a skin external preparation or a cosmetic composition, the stem cell-derived exosomes contained as an active ingredient in the composition exhibits remarkable effects on the strengthening of skin barrier or the improvement of skin barrier function and can overcome the safety problem of stem cells themselves or the conditioned media of stem cells. Thus, the stem cell-derived exosomes contained in the composition for strengthening skin barrier or improving skin barrier function according to the present invention exhibits the effect of strengthening skin barrier or improving skin barrier function by a mechanism which is completely different from the mechanism of limited wrinkle amelioration and skin regeneration known in the conventional art, and it is to be understood that this effect is not at all predictable from the conventional art.

The composition for strengthening skin barrier or improving skin barrier function according to one embodiment of the present invention comprises stem cell-derived exosomes as an active ingredient.

In the composition according to one embodiment of the present invention, the exosomes may reduce transepidermal water loss (TEWL) and increase skin hydration.

In the composition according to one embodiment of the present invention, the exosomes may increase the production of at least one selected from the group consisting of ceramides, dihydroceramides and sphingoid bases in the skin.

Specifically, the exosomes may increase the production of at least one selected from the group consisting of C16 ceramide, C18 ceramide, C20 ceramide, C22 ceramide, C24 ceramide and C24:1 ceramide, and the amount of total ceramides in the skin. In addition, the exosomes may increase the production of at least one selected from the group consisting of C16 dihydroceramide, C18 dihydroceramide, C22 dihydroceramide, C24 dihydroceramide and C24:1 dihydroceramide, and the amount of total dihydroceramides in the skin. Additionally, the exosomes may increase the production of at least one of sphingosine-1-phosphate (S1P) or sphingosine in the skin.

In the composition according to one embodiment of the present invention, the exosomes may increase the activity of sphingosine kinase 1 (SPHK1) in the skin, and decrease the activity of sphingosine-1-phosphate (S1P) lyase in the skin, which is an enzyme that degrades sphingosine 1-phosphate (S1P) of a sphingoid base.

In the composition according to one embodiment of the present invention, the exosomes may decrease the expression or production of thymic stromal lymphopoietin (TSLP), interleukin-4 (IL-4) and interleukin-13 (IL-13) in the skin.

The composition according to one embodiment of the present invention may be a pharmaceutical composition. For example, the pharmaceutical composition may be prepared as an injectable formulation.

The composition according to one embodiment of the present invention may be a cosmetic composition or a skin external preparation. For example, the cosmetic composition may be cream or lotion.

The composition according to one embodiment of the present invention may be effectively used for the prevention, suppression, alleviation or amelioration of impaired skin barrier function caused by various factors.

The composition according to one embodiment of the present invention may be prepared as a pharmaceutical composition. When the composition according to one embodiment of the present invention is prepared as a pharmaceutical composition, the composition according to one embodiment of the present invention may be any formulation for oral or parenteral administration.

The pharmaceutical composition according to one embodiment of the present invention may include pharmaceutically acceptable carriers, excipients or diluents according to a conventional method. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. For use, the pharmaceutical composition according to one embodiment of the present invention may be formulated as oral dosage forms, such as powders, pills, tablets, capsules, suspensions, emulsions, syrups, granules, elixirs, aerosols, or the like, skin external preparations, suppositories, or sterile injectable solutions.

Administration of the pharmaceutical composition according to one embodiment of the present invention means introducing a desired substance into a patient by any appropriate method, and the pharmaceutical composition may be administered by any general route, as long as the substance can reach a target tissue. For example, the pharmaceutical composition according to one embodiment of the present invention may be administered orally or parenterally. Routes for parenteral administration may include transdermal administration, intraperitoneal administration, intravenous administration, intra-arterial administration, intralymphatic administration, intramuscular administration, subcutaneous administration, intradermal administration, topical administration, intrarectal administration, and the like. However, the scope of the present invention is not limited thereto, and various administration methods known in the art are not excluded. Furthermore, the pharmaceutical composition according to one embodiment may be administered by any device through which an active ingredient may be delivered into a target tissue or cell. In addition, the effective amount of the pharmaceutical composition according to one embodiment of the present invention means the amount required for administration in order to achieve the effect of treating a disease.

Formulations for parenteral administration of the pharmaceutical composition according to the present invention may be sterilized aqueous solutions, non-aqueous solutions, suspensions, emulsions, lyophilized formulations, or suppositories. Formulations for parenteral administration of the pharmaceutical composition according to one embodiment of the present invention may also be prepared as injectable formulations. Injectable formulations according to one embodiment of the present invention may be aqueous injectable formulations, non-aqueous injectable formulations, aqueous suspension injections, non-aqueous suspension injections, solid injectable formulations which are used after dissolution or suspension, etc., but are not limited thereto. An injectable formulation according to one embodiment of the present invention may further comprise at least one of distilled water for injection, vegetable oils (e.g., peanut oil, sesame oil, camellia oil, etc.), monoglyceride, diglyceride, propylene glycol, camphor, estradiol benzoate, bismuth subsalicylate, arsenobenzol sodium, streptomycin sulfate, depending on the type thereof, and may optionally further comprise a stabilizer or a preservative.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the kind of patient's disease, the severity of disease, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

Meanwhile, when the composition according to one embodiment of the present invention is prepared as a skin external preparation and/or a cosmetic composition, it may suitably contain components which are generally used in cosmetic products or skin external preparations, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the skin external preparation and/or the cosmetic composition according to one embodiment of the present invention may include, in addition to exosomes derived from stem cells, an agent for strengthening skin barrier or improving skin barrier function and/or a moisturizer, which is used in the art, within the range that does not impair the effect of exosomes derived from stem cells, that is, the effect of strengthening skin barrier or improving skin barrier function, etc. For example, the exosomes of the present invention may be contained in or mixed with at least one of hydrogel, hyaluronic acid, salt of hyaluronic acid (e.g., sodium hyaluronate, etc.), or hyaluronate gel. In the skin external preparation and/or the cosmetic composition according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, *cassia* gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The skin external preparation and/or the cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the skin external preparation and/or the cosmetic composition may be applied to or soaked in at least one surface of a patch, a mask pack or a mask sheet.

When the skin external preparation according to one embodiment of the present invention is prepared as a cosmetic composition, it is used for the purpose of strengthening skin barrier, improving skin barrier function and/or moisturizing skin, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The skin external preparation and/or the cosmetic composition according to one embodiment of the present invention contains components which are commonly used in skin external preparations and/or cosmetic products. For example, the skin external preparation and/or the cosmetic composition may contain conventional adjuvants and carriers, such as antioxidants, stabilizers, solubilizers, vitamins, pigments, and fragrances. In addition, other components in each formulation for the skin external preparation and/or the cosmetic composition may be suitably selected without difficulty by those skilled in the art depending on the type or intended use of the skin external preparation and/or the cosmetic composition.

Another embodiment of the present invention provides a cosmetic method for regulating mammalian skin conditions, except for treatment purposes, by strengthening skin barrier or improving skin barrier function using the composition for strengthening skin barrier or improving skin barrier function. In the cosmetic method of the present invention, the expression "regulating skin conditions" means improving skin conditions and/or prophylactically regulating skin conditions, and the expression "improving skin conditions" means a visually and/or tactilely perceivable positive change in the appearance and feeling of skin tissue. For example, the expression "improving skin conditions" may include improving skin moisturization, improving skin smoothness, preventing dry skin, preventing skin trouble, reducing skin redness, and the like.

The cosmetic method according to one embodiment of the present invention includes: (a) applying the composition for strengthening skin barrier or improving skin barrier function directly to a mammalian skin; or (b) contacting or attaching a patch, a mask pack or a mask sheet, which has the composition for strengthening skin barrier or improving skin barrier function applied thereto or soaked therein, to the mammalian skin; or sequentially performing (a) and (b). In step (a), the composition for strengthening skin barrier or improving skin barrier function may be lotion or cream.

Alternatively, the cosmetic method according to one embodiment of the present invention may further comprise (c) removing the patch, mask pack or mask sheet from the mammalian skin after step (b), and applying the composition for strengthening skin barrier or improving skin barrier function to the mammalian skin. In step (c), the composition for strengthening skin barrier or improving skin barrier function may be lotion or cream.

Still another embodiment of the present invention provides a method for preventing, suppressing, alleviating, ameliorating or treating a skin disease caused by impaired skin barrier function, the method comprising administering to a mammal a therapeutically effective amount of the pharmaceutical composition. The mammal may be humans, dogs, cats, rodents, horses, cattle, monkeys, or pigs.

Advantageous Effects

The composition for strengthening skin barrier or improving skin barrier function according to the present invention is able to improve objective indicators related to the protection of skin barrier, the strengthening of skin barrier, and/or the improvement of skin barrier function. The composition according to the present invention is able to improve the indicator of loss of moisture in stratum corneum, for example, transepidermal water loss (TEWL), and increase skin hydration.

In addition, the composition according to the present invention exhibits the effects of increasing the amount of ceramides, dihydroceramides and/or sphingoid bases, increasing the activities of enzymes that are involved in the synthesis thereof, and decreasing the activities of enzymes that are involved in the degradation thereof.

Further, the composition according to the present invention is able to restore skin barrier function by reducing TSLP, IL-4, and IL-13 which are closely associated with skin barrier damage, and thus interrupting a vicious circle in which the lipids and proteins contributing to skin barrier decrease.

Therefore, the composition according to the present invention is useful as a pharmaceutical composition, a skin external preparation and a cosmetic composition for strengthening skin barrier or improving skin barrier function.

It should be understood that the scope of the present is not limited to the aforementioned effects.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A to 1E show the results of analyzing the physical properties of exosomes obtained according to one embodiment of the present invention. "FIG. 1A" shows the particle size distribution and the number of particles obtained by tunable resistive pulse sensing (TRPS) analysis. "FIG. 1B" shows the particle size distribution and the number of particles obtained by nanoparticle tracking analysis (NTA). "FIG. 1C" shows different magnifications of particle images obtained by transmitted electron microscopy (TEM) analysis. "FIG. 1D" shows the results of Western blot analysis of exosomes obtained according to one embodiment of the present invention. "FIG. 1E" shows the results of flow cytometry of CD63 and CD81 in the analysis of markers for exosomes obtained according to one embodiment of the present invention.

In FIG. 4, PBS denotes phosphate-buffered saline; DEX denotes dexamethasone; EXO denotes exosomes; CM denotes conditioned media of adipose-derived stem cells; and CM-EXO denotes exosome-depleted conditioned media of adipose-derived stem cells.

In FIG. 5, PBS denotes phosphate-buffered saline; DEX denotes dexamethasone; and each number represents the amount of exosomes (μg/mL) used for treatment.

FIG. 6A shows the results of NTA analysis of exosomes isolated by a conventional precipitation method; FIG. 6B shows the results of NTA analysis of exosomes isolated by the method according to one embodiment of the present invention; and FIG. 6C is a graph comparing the NO formation-reducing effects. The extent of reduction in NO formation was expressed as a relative ratio (%) to the extent of reduction in NO formation by dexamethasone (Dex) as a positive control.

FIG. 12A shows that the amount of sphingosine-1-phosphate (S1P) increased in the skin, and FIG. 12B shows that the amount of sphingosine increased in the skin.

FIG. 15 shows tissue section images obtained after staining the skin tissue of each group with toluidine blue.

EXAMPLES

Figure 1A:
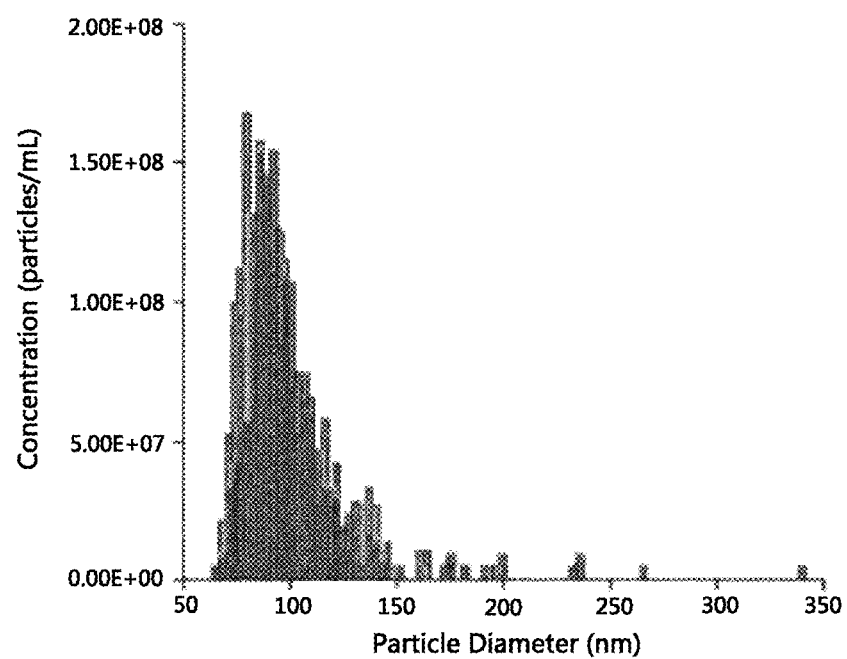

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Cell Culture

RAW 264.7 cells (mouse macrophage cell line) were purchased from the Korean Cell Line Bank and cultured. For cell culture, cells were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$.

Human dermal fibroblast (HDF) HS68 cells purchased from ATCC were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$.

According to a cell culture method known in the technical field to which the present invention pertains, adipose-derived stem cells were cultured at 37° C. under 5% $CO_2$. Next, the cells were washed with phosphate-buffered saline (purchased from ThermoFisher Scientific), and then the medium was replaced with serum-free, phenol red-free medium, and the cells were cultured for 1 to 10 days. The supernatant (hereinafter, referred to as "conditioned medium (CM)") was recovered.

In order to obtain exosomes having a uniform particle size distribution and high purity in an exosome isolation process, 2 wt % of trehalose was added to the conditioned medium. After addition of trehalose, the conditioned medium was filtered through 0.22 μm filter to remove impurities, such as cell debris, waste, macroparticles and the like. From the filtered conditioned medium, exosomes were immediately isolated. In addition, the filtered conditioned medium was stored in a refrigerator (10° C. or below), and then used for exosome isolation. Furthermore, the filtered conditioned medium was freeze-stored in an ultra-low temperature freezer at −60° C. or below, thawed, and then subjected to exosome isolation. Thereafter, exosomes were isolated from the conditioned medium by TFF.

Example 2: Isolation and Purification of Exosomes by TFF Method

For isolating, concentrating and diafiltrating exosomes from the conditioned medium filtered through 0.22 μm filter in Example 1, TFF method was used. As a filter for TFF method, a cartridge filter (also known as a hollow fiber filter; purchased from GE Healthcare) or a cassette filter (purchased from Pall, Sartorius or Merck Millipore) was used. The TFF filter may be selected with various molecular weight cutoffs (MWCOs). Using the filter having selected MWCO, exosomes were isolated and concentrated, and particles, proteins, lipids, nucleic acids, low-molecular-weight compounds, etc., were removed, which are smaller than the MWCO.

To isolate and concentrate exosomes, a TFF filter having MWCO of 100,000 Da (Dalton), 300,000 Da or 500,000 Da was used. Exosomes were isolated from the conditioned medium by removing substances smaller than the MWCO and concentrating the conditioned medium to a volume of about 1/100 to 1/25 by the TFF method.

The isolated and concentrated solution of exosomes was additionally subjected to diafiltration. The diafiltration was performed continuously (continuous diafiltration) or discontinuously (discontinuous diafiltration), using a buffer having at least 4 times, preferably at least 6 to 10 times, more preferably at least 12 times volume of the isolated exosomes. To obtain exosomes having a uniform particle size distribution and high purity, 2 wt % trehalose in PBS was added to the buffer.

Example 3: Analysis of Characteristics of Isolated Exosomes

Figure 1B:
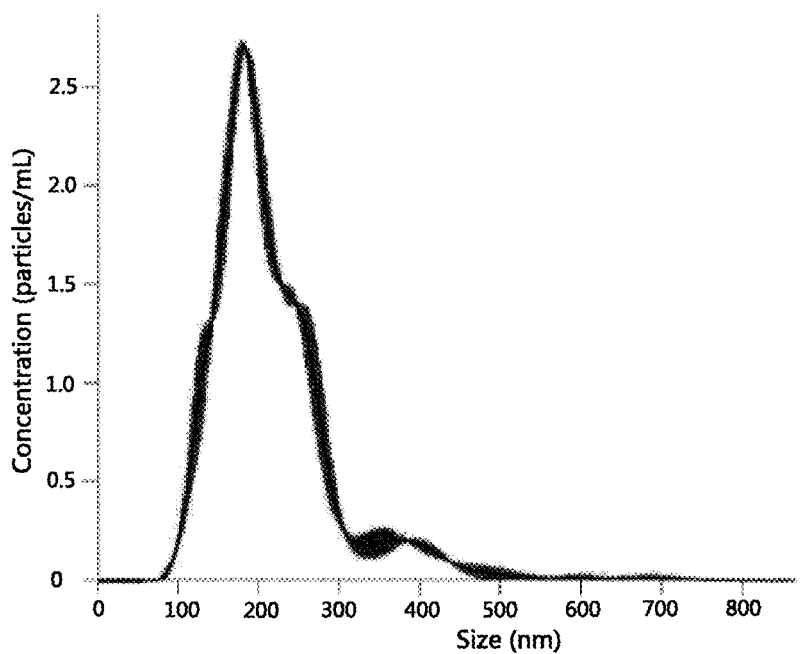

The particle size and concentration of the isolated exosomes were measured by nanoparticle tracking analysis (NTA; purchased from Malvern) or tunable resistive pulse sensing (TRPS; purchased form Izon Science). The uniformity and size of the isolated exosomes were analyzed using transmitted electron microscopy (TEM). The results of TRPS, NTA and TEM analyses of the exosomes isolated according to one embodiment of the present invention are shown in FIGS. 1A to 1C.

Figure 1D:
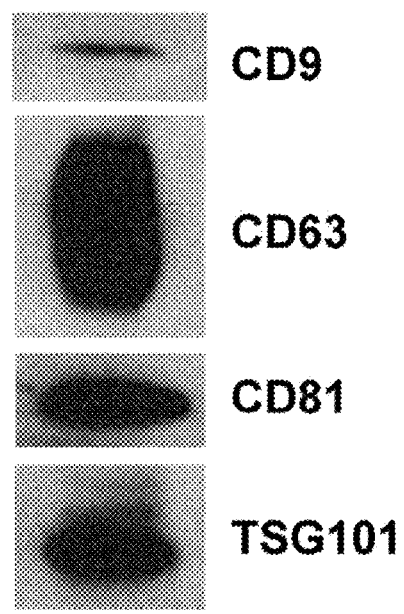

FIG. 1D shows the results of Western blot analysis of the exosomes isolated by the isolation method according to one embodiment of the present invention. As shown therein, the presence of CD9, CD63, CD81 and TSG101 markers was confirmed. As antibodies for each of the markers, anti-CD9 (purchased from Abcam), anti-CD63 (purchased from System Biosciences), anti-CD81 (purchased from System Biosciences), and anti-TSG101 (purchased from Abcam) were used, respectively.

FIG. 1E shows the results of flow cytometry of the exosomes isolated by the isolation method according to one embodiment of the present invention. As shown therein, the presence of CD63 and CD81 markers was confirmed. To isolate CD63-positive exosomes, an Exosome-Human CD63 Isolation/Detection Reagent kit (purchased from ThermoFisher Scientific) was used according to the manufacturer's instruction. The markers were stained with PE-Mouse anti-human CD63 (purchased from BD) or PE-Mouse anti-human CD81 (purchased from BD), and then analyzed using a flow cytometer (ACEA Biosciences).

Meanwhile, it is to be understood that the stem cell-derived exosomes that are used in the present invention are not limited to the exosomes of the Examples as described above, it is possible to use exosomes derived from a variety of stem cells that are being used in the art or can be used in the future. In addition, it should be noted that the stem cell-derived exosomes isolated according to the above Examples should be understood as an example of stem cell-derived exosomes that may be used in the present invention, and the scope of the present invention is not limited thereto.

Example 4: Measurement of Cytotoxicity Following Exosome Treatment

In order to evaluate the cytotoxicity of exosomes, isolated by the isolation method according to one embodiment of the present invention, in human dermal fibroblast HS68 cells, the cells were treated with various concentrations of the exosomes, and the proliferation rate of the cells was examined. HS68 cells were suspended in 10% FBS-containing DMEM, and then seeded resulting in 80 to 90% confluency and cultured in an incubator at 37° C. under 5% $CO_2$ for 24 hours. After 24 hours, the medium was removed, and the cells were treated with various concentrations of the exosomes prepared in Example 2. Then, the viability of the cells was evaluated while the cells were cultured for 24 to 72 hours. The cell viability was measured using WST-1 reagent (purchased from Takara), MTT reagent (purchased from Sigma), CellTiter-Glo reagent (purchased from Promega) or alamarBlue reagent (purchased from ThermoFisher Scientific) with a microplate reader (purchased from Molecular Devices).

Figure 2:
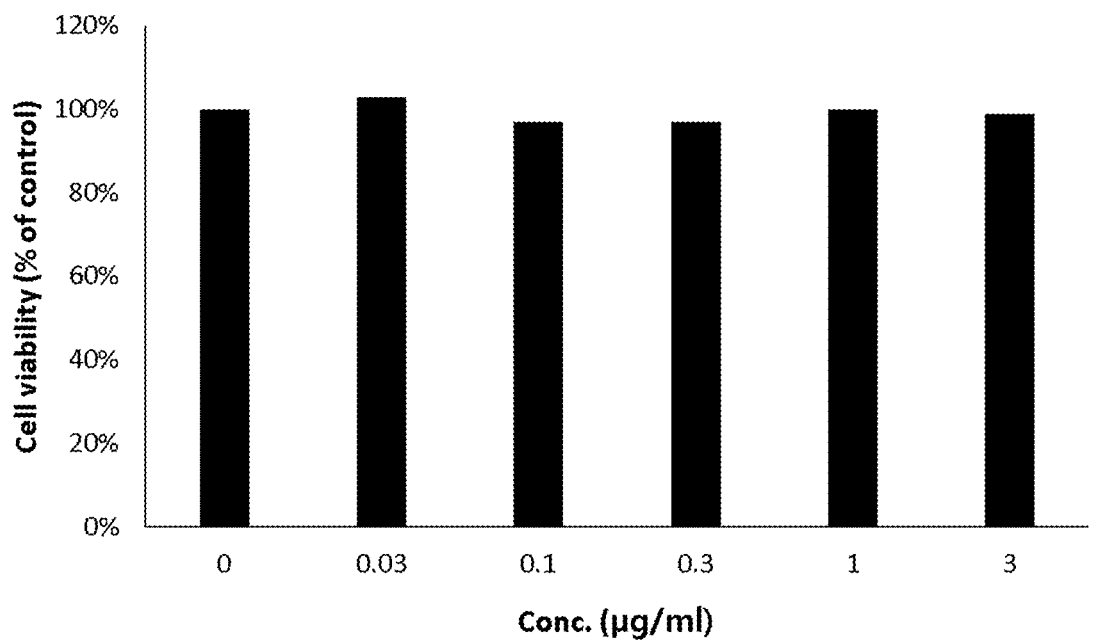
FIG. 2 shows results indicating that exosomes according to one embodiment of the present invention were not cytotoxic when human dermal fibroblast HS68 cells were treated with the exosomes.

As a control, the cells cultured in conventional cell culture medium not treated with the exosomes was used. It was confirmed that the exosomes of the present invention showed no cytotoxicity in the concentration range used in the test (FIG. 2).

Example 5: Measurement of Inflammatory Response Using Microphage Cell Line

RAW 264.7 cells were suspended in 10% FBS-containing DMEM medium, and seeded into each well of a multiwell plate resulting in 80 to 90% confluency. Next day, the cells were treated and cultured with a suitable concentration of the exosomes of the present invention (exosomes prepared in Example 2) diluted in fresh serum-free medium containing LPS for 1 to 24 hours. After completion of the culture, the culture supernatant was collected, and NO and inflammatory cytokines present in the culture medium were measured to examine inflammatory response. Inflammatory response in the culture medium was measured using an NO detection kit (purchased from Intronbio or Promega). The amounts of the inflammatory cytokine TNF-α in the group treated with LPS alone and the group treated with LPS together with the exosomes of the present invention were measured using an ELISA kit (purchased from R&D system) according to the manufacturer's manual. As a positive control, cells were treated with dexamethasone (purchased from Sigma). In addition, cDNA was prepared from the total RNA obtained from RAW 264.7 cells treated as described above, and changes in the mRNA expression levels of iNOS, TNF-α, IL-6 and IL-1β were measured using a real-time PCR method. As a reference gene for normalizing the above genes, GAPDH gene was used. The sequences of primers used in the real-time PCR are shown in Table 1 below.

TABLE 1

Nucleotide sequences of primers used in real-time PCR

| Genes | Forward primer (5' → 3') | Reverse Primer (5' → 3') |
|---|---|---|
| TNF-α | TCT CAT CAG TTC TAT GGC CCA GAC (SEQ ID NO: 1) | GGC ACC ACT AGT TGG TTG TCT TTG (SEQ ID NO: 2) |
| iNOS | GCT ACC ACA TTG AAG AAG CTG GTG (SEQ ID NO: 3) | CCA TAG GAA AAG ACT GCA CCG AAG (SEQ ID NO: 4) |
| GAPDH | GAC ATC AAG AAG GTG GTG AAG CAG (SEQ ID NO: 5) | CCC TGT TGC TGT AGC CGT ATT CAT (SEQ ID NO: 6) |
| IL-6 | GCC AGA GTC CTT CAG AGA GAT ACA (SEQ ID NO: 7) | ATT GGA TGG TCT TGG TCC TTA GCC (SEQ ID NO: 8) |
| IL-1β | GCA ACG ACA AAA TAC CTG TGG CCT (SEQ ID NO: 9) | AGT TGG GGA ACT CTG CAG ACT CAA (SEQ ID NO: 10) |

Figure 3:
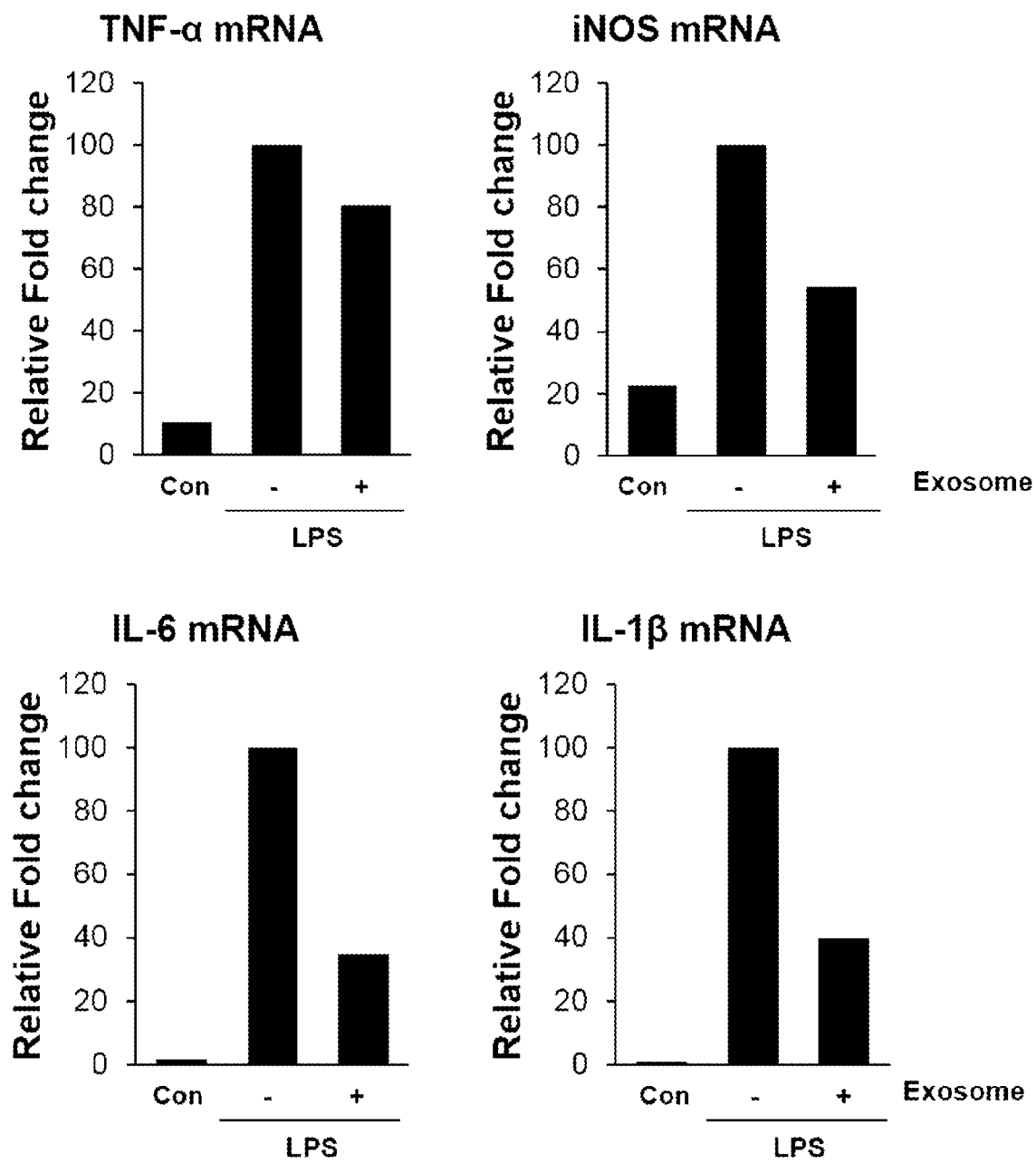
FIG. 3 shows graphs obtained by real-time PCR results indicating that LPS-induced expressions of TNF-α, IL-6, IL-1β and iNOS mRNA decreased when RAW 264.7 cells were treated with LPS and the exosomes of the present invention.
Figure 4:
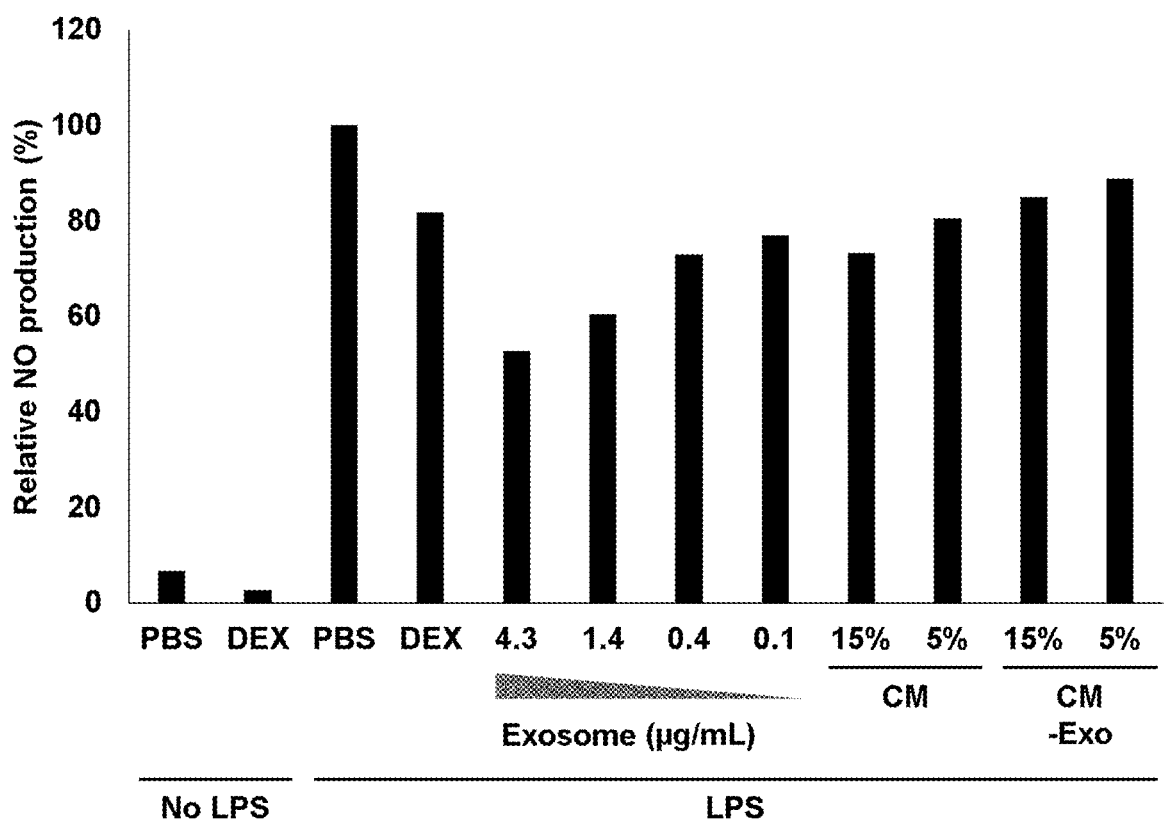
FIG. 4 shows experimental results indicating that the exosomes according to one embodiment of the present invention have the effect of reducing NO formation, a kind of inflammatory reaction.
Figure 5:
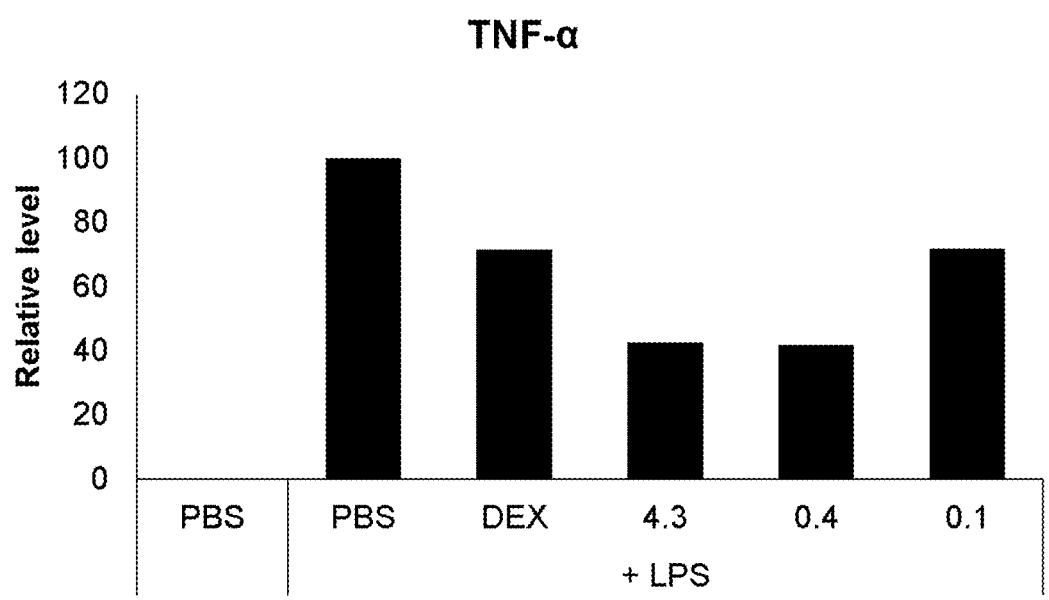
FIG. 5 shows experimental results indicating that the exosomes according to one embodiment of the present invention have the effect of reducing the formation of TNF-α, an inflammatory cytokine.

First, as shown in FIG. 3, when mouse macrophage RAW 264.7 cells were treated with exosomes of the present invention together with LPS, the mRNA expression levels of the LPS-induced inflammatory cytokines TNF-α, IL-6 and IL-1β decreased, and the mRNA expression level of iNOS (NO producing enzyme) decreased. Next, as shown in FIG. 4, it was confirmed that when mouse macrophage RAW 264.7 cells were treated with exosomes of the present invention under the presence of LPS, NO production, an LPS-induced inflammatory response, decreased in a concentration-dependent manner. In addition, as shown in FIG. 5, it was confirmed that when mouse macrophage RAW 264.7 cells were treated with exosomes of the present invention under the presence of LPS, the production of the LPS-induced inflammatory cytokine TNF-α decreased.

These results suggest that the exosomes of the present invention can prevent, suppress, alleviate or repair impaired skin barrier function caused by inflammatory response. Accordingly, it is considered that the composition for strengthening skin barrier or improving skin barrier function according to the present invention is useful for the protection of skin barrier, the strengthening of skin barrier, or the improvement of skin barrier function.

Example 6: Comparison of NO Formation-Reducing Effect Between Isolation Methods

Figure 6A:
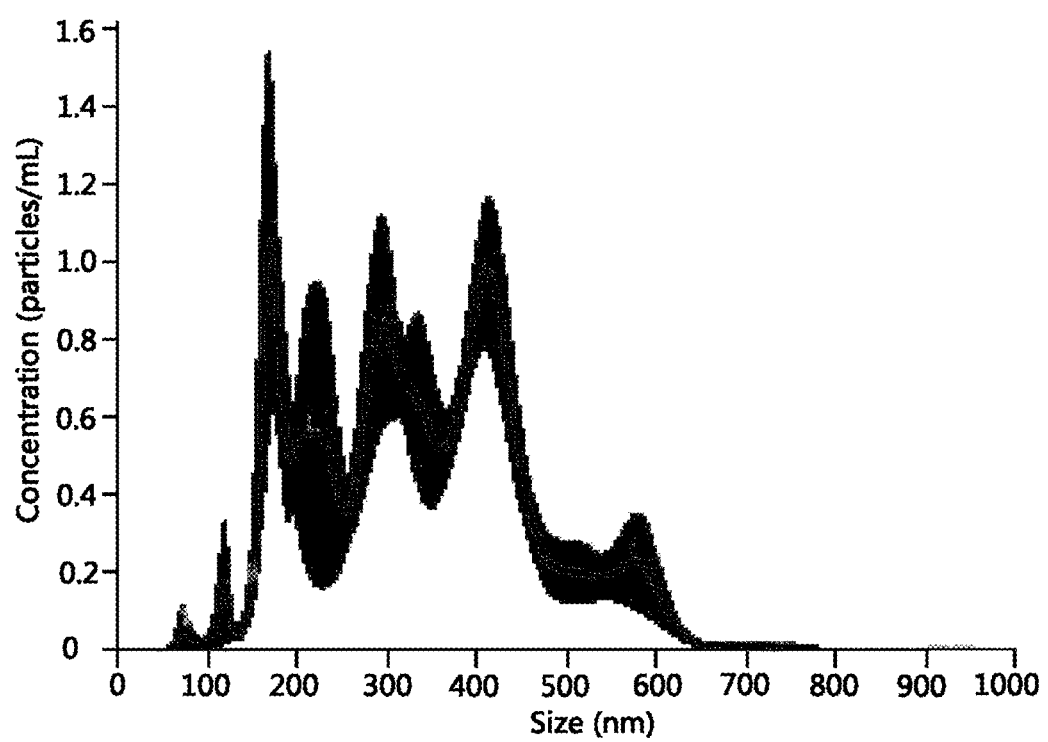
FIGS. 6A to 6C show experimental results comparing the NO formation-reducing effect of exosomes isolated according to one embodiment of the present invention, with the NO formation-reducing effect of exosomes isolated by a conventional precipitation method (PPT).
Figure 6B:
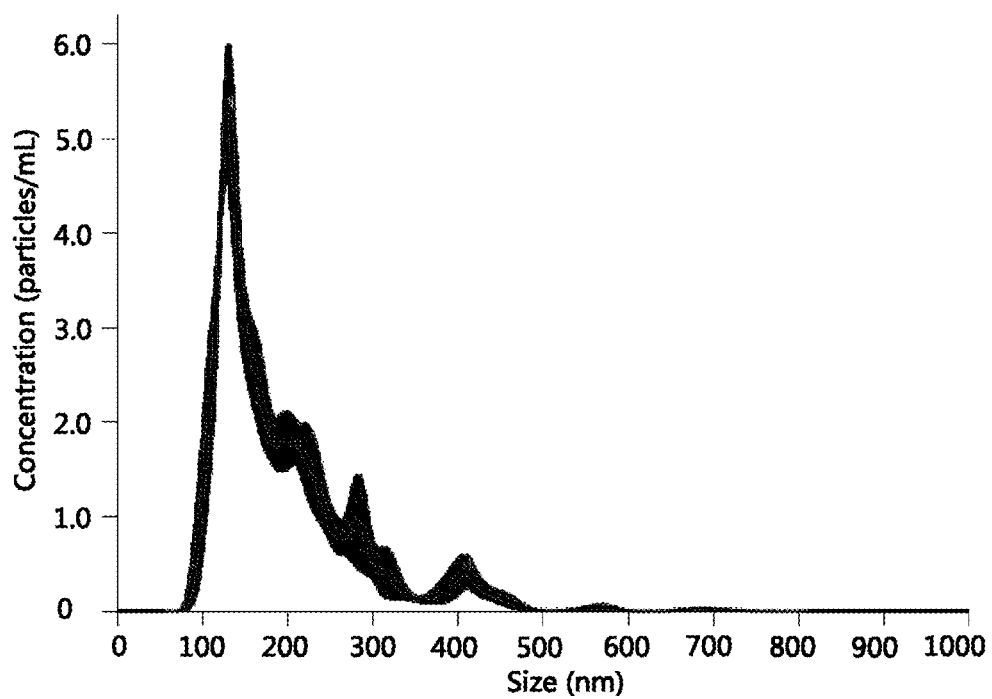
Figure 6C:
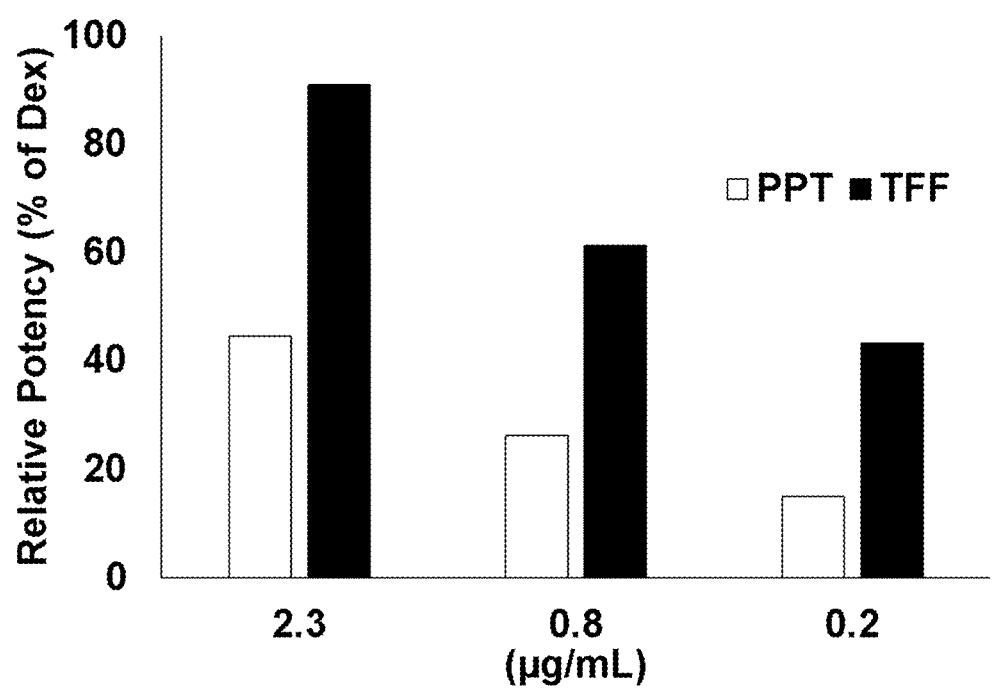

To compare NO formation-reducing effect of exosomes between isolation methods, exosomes isolated by a conventional precipitation method were prepared besides the exosomes obtained by the TFF isolation and purification according to one embodiment of the present invention. The precipitation method was performed according to the protocol of the manufacturer (System Biosciences). It was confirmed that the exosomes isolated by the conventional precipitation method (see FIG. 6A) had a lower uniformity of the particle size distribution and various particle sizes as compared with the exosomes isolated and purified by the TFF method of one embodiment of the present invention (see FIG. 6B). In addition, as shown in FIG. 6C, it was confirmed that the exosomes isolated and purified by the TFF method of one embodiment of the present invention inhibited NO formation at a remarkably higher level than the exosomes obtained by the conventional precipitation method. These results show that the exosomes isolated and purified according to one embodiment of the present invention are superior to the exosomes isolated according to the conventional method, in terms of the uniformity of particle size distribution and the inhibition of NO formation.

Accordingly, it is considered that the exosomes obtained according to the isolation method of one embodiment of the present invention have excellent performance or functional activities (for example, uniformity of particle size distribution, inhibition of NO production, reduction of inflammatory response, etc.) as compared with exosomes obtained according to a conventional isolation method, and the composition for strengthening skin barrier or improving skin barrier function according to the present invention, which contains, as an active ingredient, the stem-cell derived exosomes having excellent functional activities as described above, is much superior to the conventional art in terms of the effect of preventing, suppressing, alleviating or repairing impaired skin barrier function caused by inflammatory response.

Example 7: Animal Model Having Skin Barrier Damage

In order to establish an animal model to be used to confirm the strengthening of skin barrier or the improvement of skin barrier function, oxazolone was used. When oxazolone is applied to the skin, it can cause damage to skin barrier function, resulting in an increase in transepidermal water loss (TEWL) and a decrease in hydration of *stratum corneum*, a decrease in the expression of loricrin, involucrin and filaggrin which are structural proteins of the skin barrier, and an increase in the pH of *stratum corneum*, thereby providing an animal model in which skin barrier function was damaged (see Journal of Investigative Dermatology (2008) 128(1), 79-86).

Female SKH-1 mouse (5-week-old; purchased from Central Laboratory Animal Inc.) were purchased, adapted for 7 days, and then used in this experiment. The adapted mice were divided into six groups as follows after skin barrier damage was induced in the mice.

Figure 7:
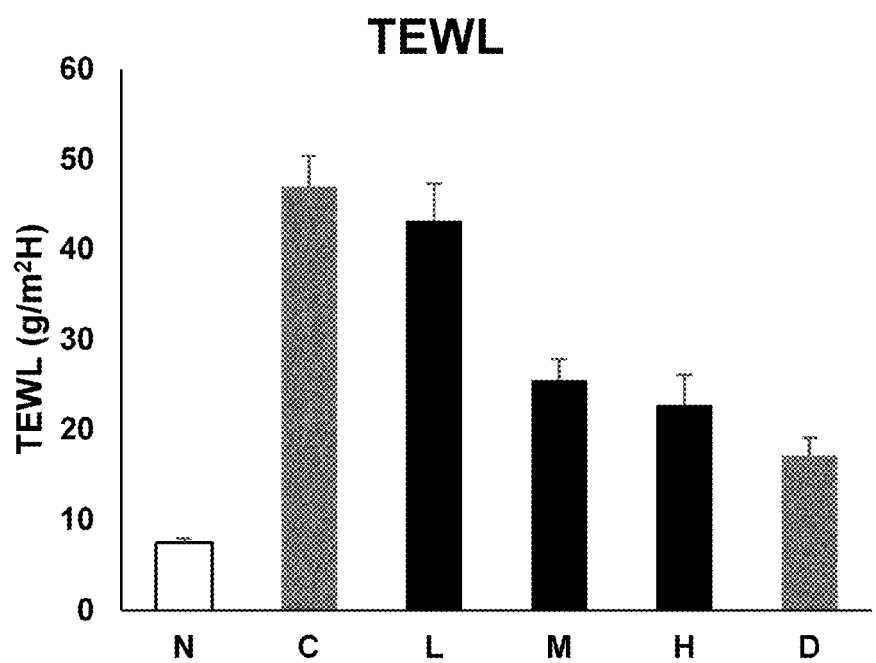
FIG. 7 depicts a graph showing that when mice, in which skin barrier damage was induced, were treated with the exosomes according to one embodiment of the present invention, transepidermal water loss (TEWL) decreased in a manner of depending on the dose of the exosomes.

(1) Normal: a normal control group (indicated by "N" in FIG. 7);
(2) Control (skin barrier damage-induced group): a negative control group in which skin barrier damage was induced by oxazolone (indicated by "C" in FIG. 7);
(3) Exosome low dose: a test group in which the exosomes prepared in Example 2 were subcutaneously (SC)

injected at a dose of 1 µg/head three times a week for four weeks, after skin barrier damage was induced by oxazolone (indicated by "L" in FIG. 7);

(4) Exosome medium dose: a test group in which the exosomes prepared in Example 2 were subcutaneously (SC) injected at a dose of 3 µg/head three times a week for four weeks, after skin barrier damage was induced by oxazolone (indicated by "M" in FIG. 7);

(5) Exosome high dose: a test group in which the exosomes prepared in Example 2 were subcutaneously (SC) injected at a dose of 10 µg/head three times a week for four weeks, after skin barrier damage was induced by oxazolone (indicated by "H" in FIG. 7); and (6) Dexamethasone: a test group (positive control group) in which 0.03% dexamethasone (purchased from Sigma) dissolved in ethanol was subcutaneously (SC) injected at a dose of 100 µg/head three times a week for four weeks, after skin barrier damage was induced by oxazolone (indicated by "D" in FIG. 7).

The mice of each of test groups (2) to (6) were sensitized by applying 200 µL of 2% oxazolone (purchased from Sigma) to the mouse back skin. After sensitization, the mice were subjected to skin barrier recovery for 5 to 7 days, and then skin barrier damage was induced by applying 100 µL of 0.025% to 0.05% oxazolone to the mouse back skin of each of test groups (2) to (6) every other day for about 15 days. In addition, in order to maintain the skin barrier damage, 100 µL of 0.025% to 0.05% oxazolone was applied to the mouse back skin of each of test groups (2) to (6) every other day during the exosome treatment period.

Before and after treatment with the exosomes of the present invention, the average water evaporation from the skin was measured using a TEWL measurement system, and the hydration of the skin was measured using a hydration measurement device (Corneometer CM825; Courage-Khazaka Electronic GmbH, Germany). The number of mice measured was 12 for each test group (n=12).

Figure 8:
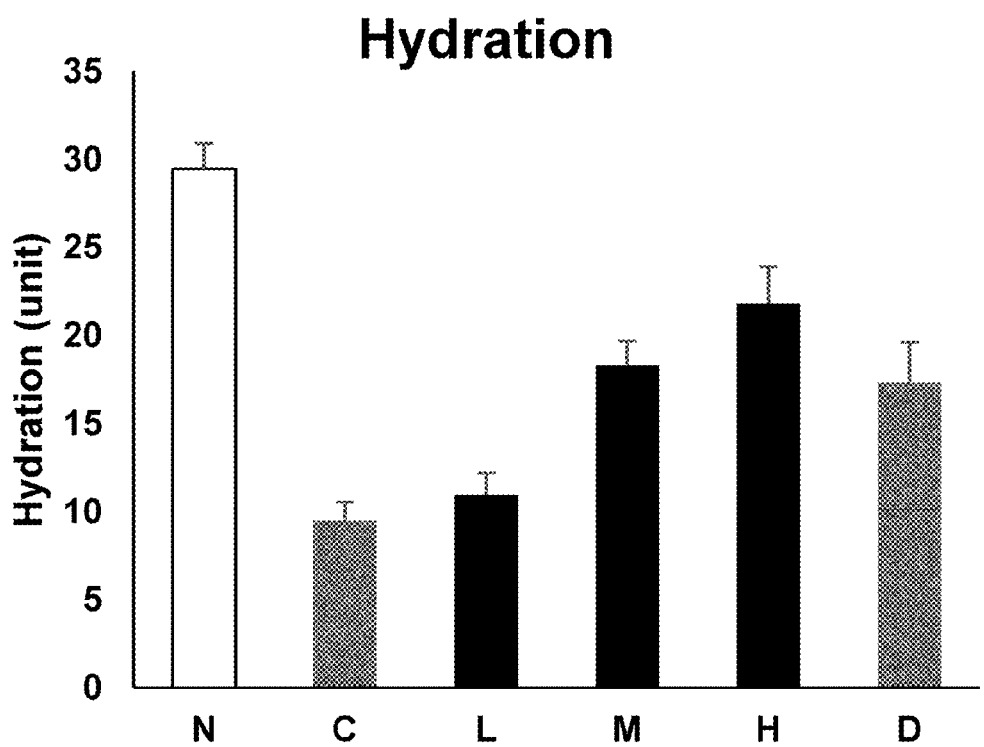
FIG. 8 depicts a graph showing that when mice, in which skin barrier damage was induced, were treated with the exosomes according to one embodiment of the present invention, skin hydration increased in a manner of depending on the dose of the exosomes.

As a result, it was confirmed that TEWL (transepidermal water loss), that is, water evaporation from *stratum corneum* in test groups (3) to (5) treated with the exosomes according to one embodiment of the present invention decreased as compared with that in the disease control group (skin barrier damage-induced group) in a manner of depending on the dose of the exosomes (FIG. 7). In addition, it was confirmed that the skin hydration in test groups (3) to (5) treated with the exosomes according to one embodiment of the present invention increased as compared with that in the disease control group in a manner of depending on the dose of the exosomes (FIG. 8). Accordingly, the composition comprising, as an active ingredient, the exosomes according to one embodiment of the present invention, is able to protect and strengthen the skin barrier to reduce water evaporation from *stratum corneum* and to increase skin hydration.

Figure 9:
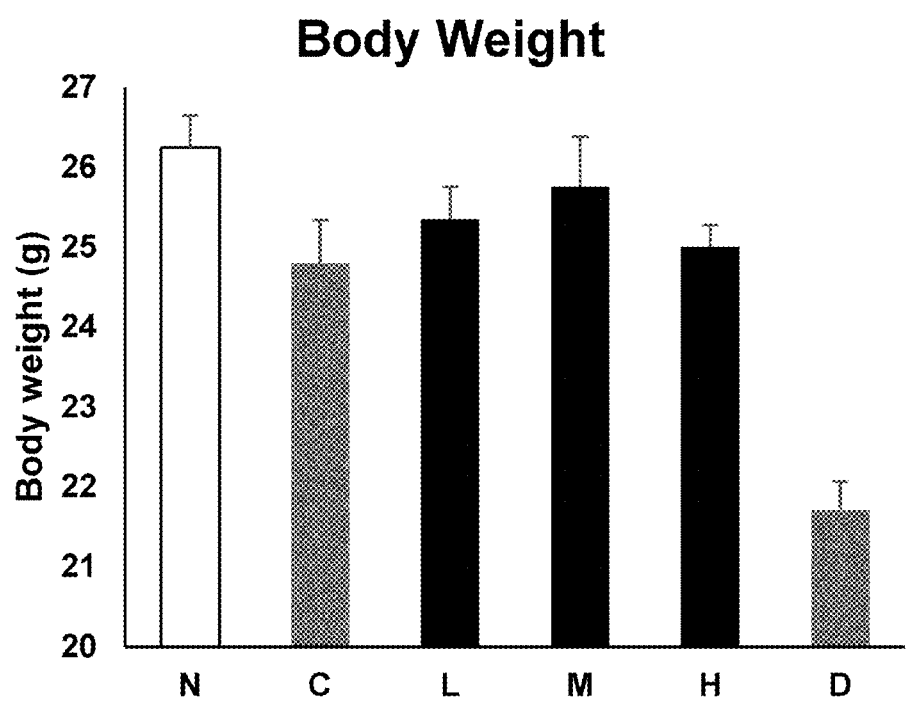
FIG. 9 depicts a graph showing the results of measuring the body weight of mice in which skin barrier damage was induced. The results indicate that a group treated with dexamethasone had body weight loss due to side effects, whereas a test group treated with exosomes according to one embodiment of the present invention, had almost no body weight loss.
Figure 10A:
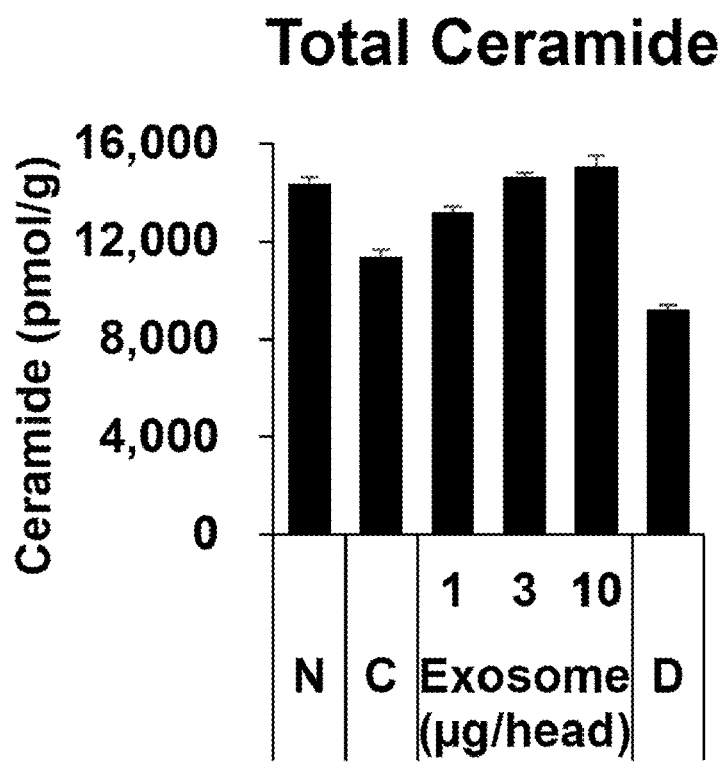
FIGS. 10A to 10G are graphs showing that when mice, in which skin barrier damage was induced, were treated with the exosomes according to one embodiment of the present invention, the amount of ceramides increased in the skin.
Figure 10B:
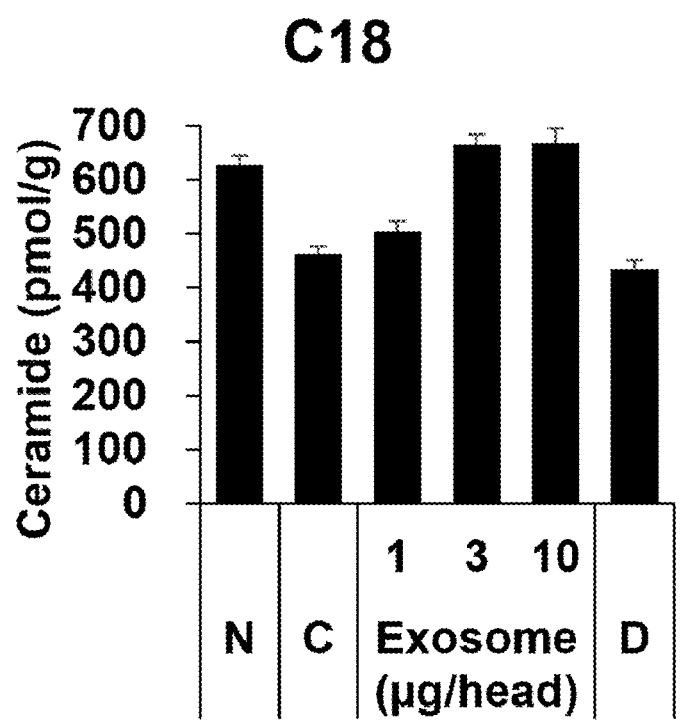
Figure 10C:
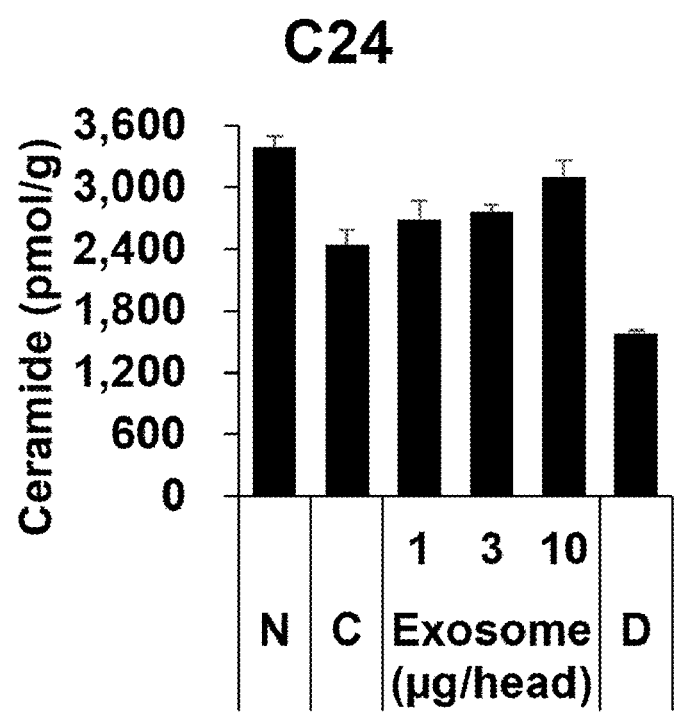
Figure 10D:
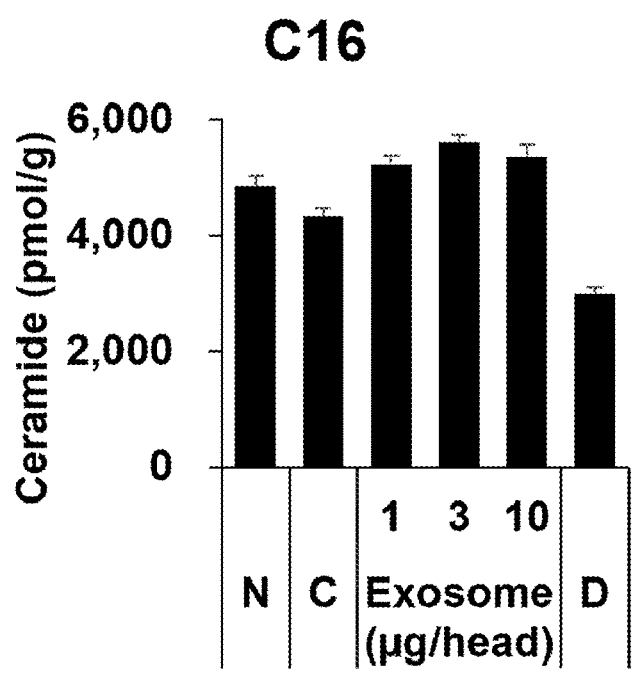
Figure 10E:
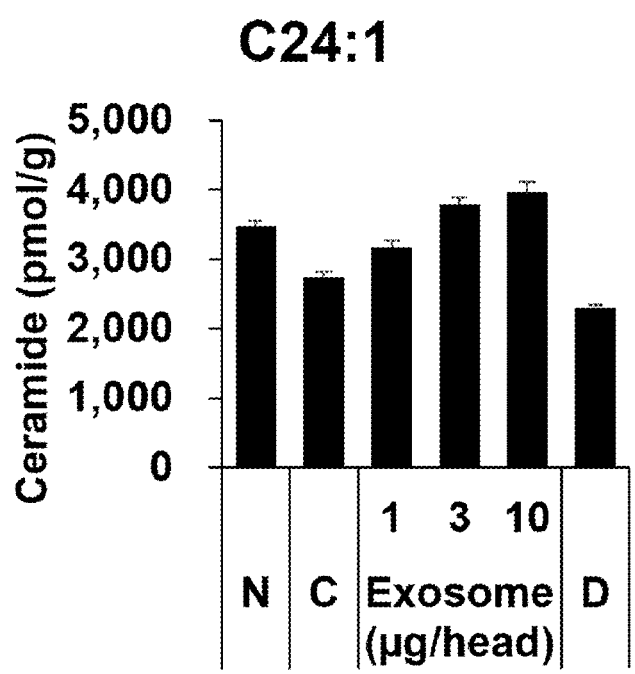
Figure 10F:
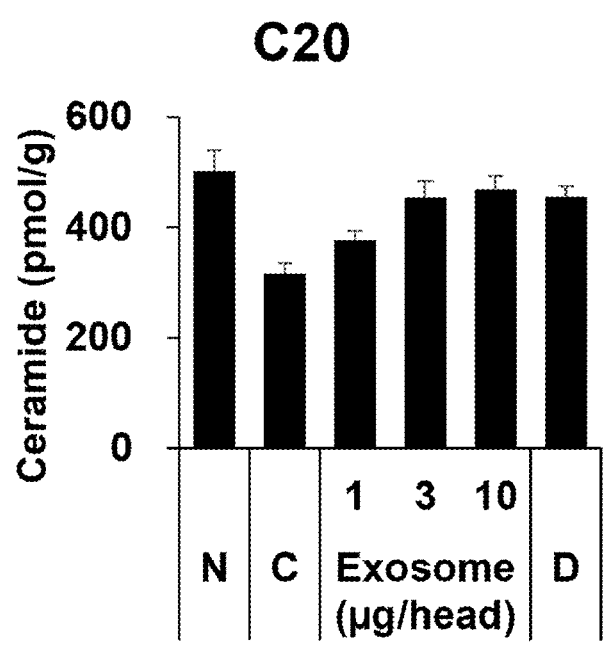
Figure 10G:
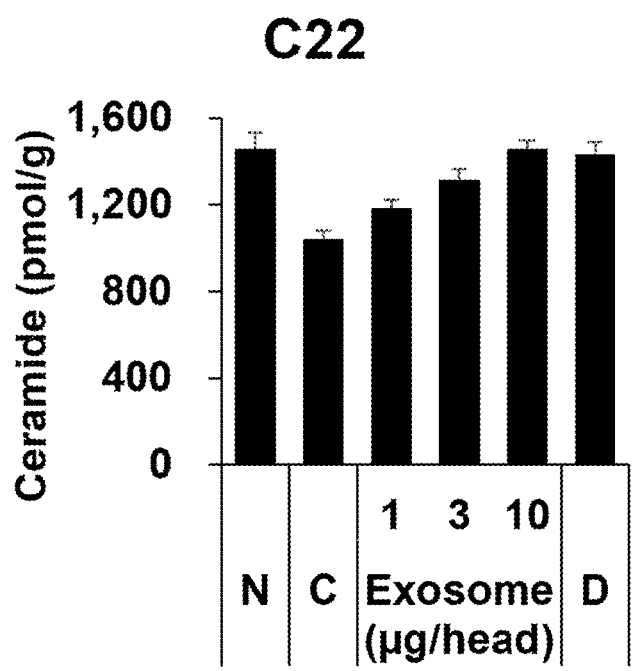
Figure 11A:
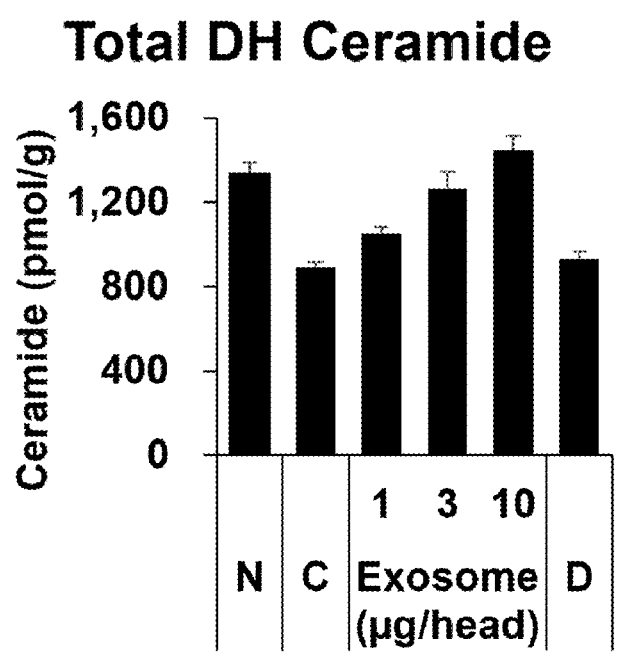
FIGS. 11A to 11F are graphs showing that when mice, in which skin barrier damage was induced, were treated with the exosomes according to one embodiment of the present invention, the amount of dihydroceramides increased in the skin.
Figure 11B:
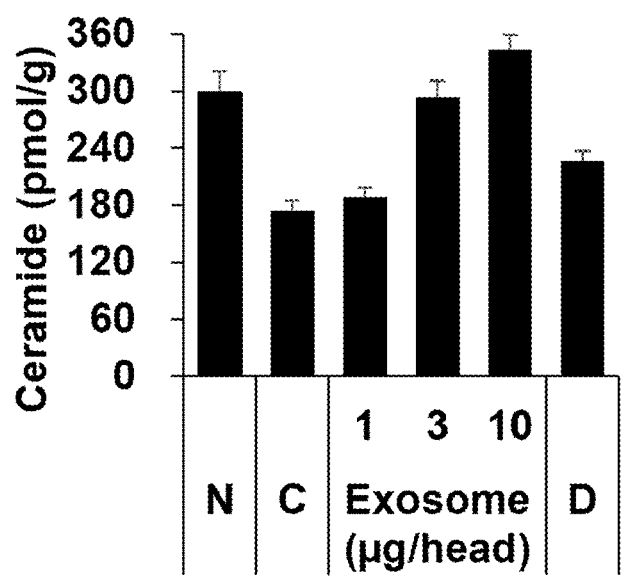
Figure 11C:
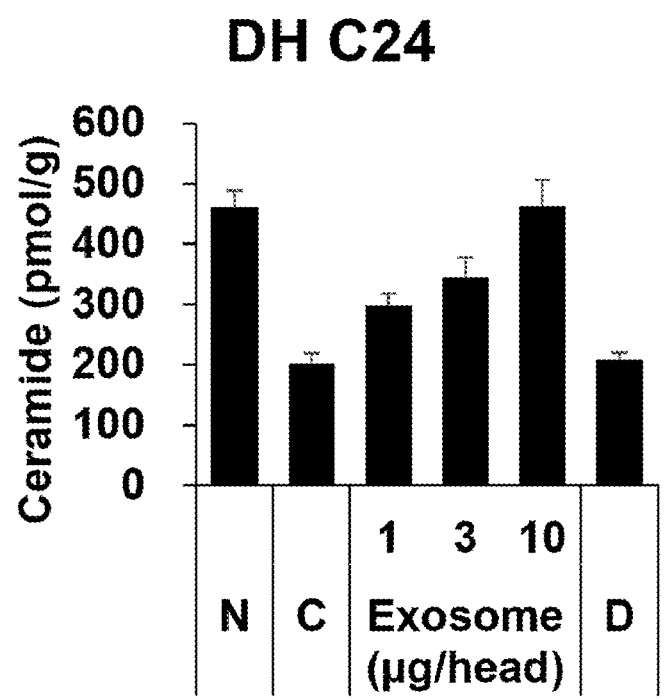
Figure 11D:
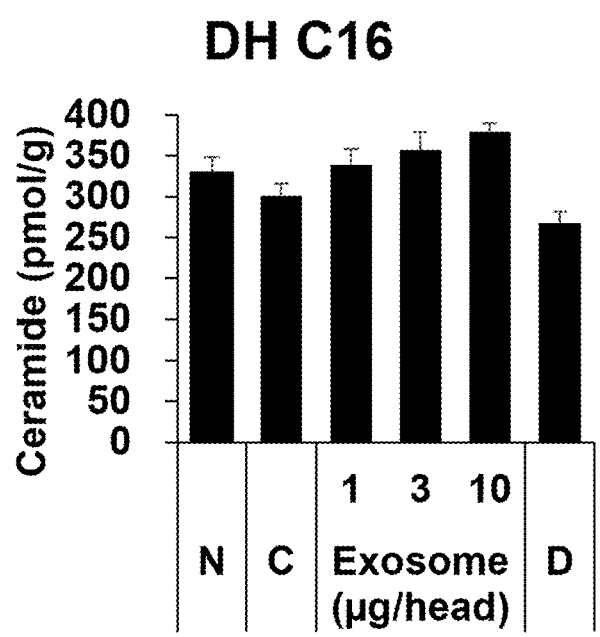
Figure 11E:
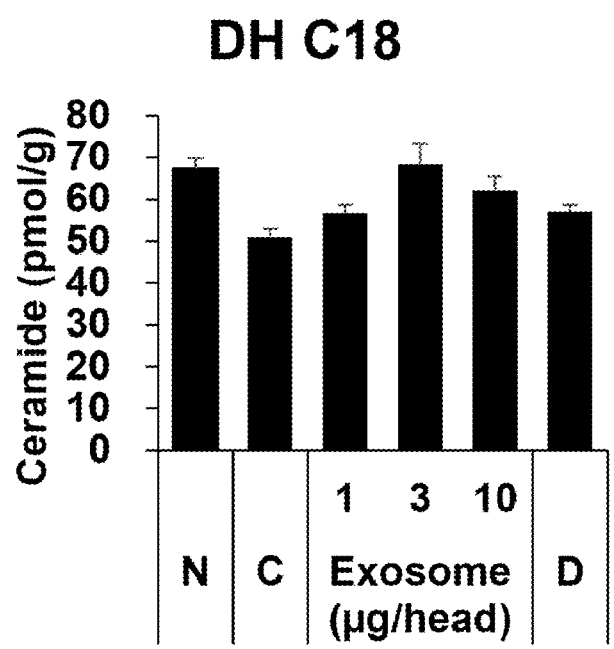
Figure 11F:
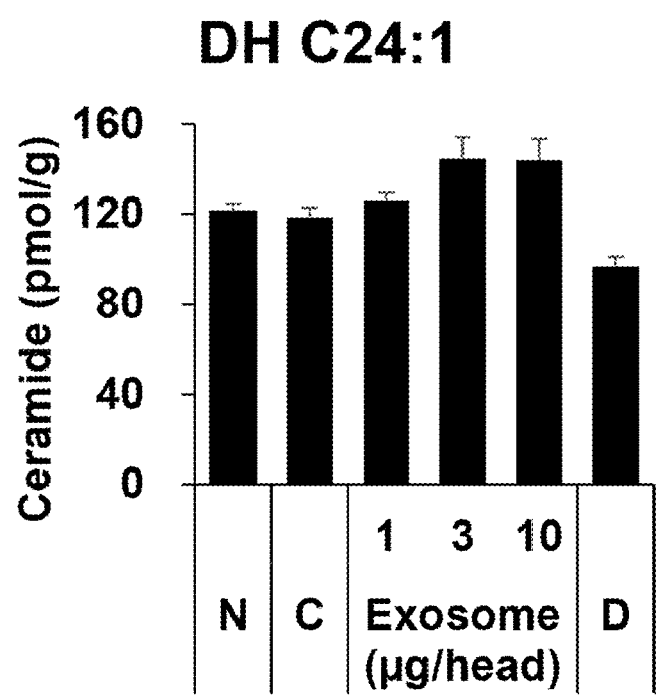

Meanwhile, the results of measuring the body weight of each test group (n=12) indicated that in test group (6) treated with dexamethasone, there was body weight loss due to side effects, but in test groups (3) to (5) treated with the exosomes according to one embodiment of the present invention, the body weight did not substantially decrease compared to the normal control group (FIG. 9). That is, dexamethasone that is generally used for the recovery or alleviation of skin barrier damage shows side effects such as body weight loss, whereas the composition comprising the exosomes as an active ingredient according to one embodiment of the present invention has advantages in that it can reduce side effects such as body weight loss while protecting and strengthening the skin barrier.

Example 8: Confirmation of Improvement of Skin Barrier Indicators

The mice of Example 7 were euthanized and their skin samples were collected. Then, for each test group, the amounts of ceramides, dihydroceramides, sphingosine and sphingosine-1-phosphate (S1P), the activity of sphingosine kinase 1 (SPHK1), and the activity of S1P lyase which is an enzyme that degrades sphingosine 1-phosphate (S1P) were measured. The number of the mice used in the measurement was 8 for each test group (n=8).

The amounts of ceramides having different carbon lengths, total ceramides, sphingosine and sphingosine-1-phosphate (S1P) were analyzed using LC-MS/MS (API 3200 Triple quadruple mass, AB/SCIEX) as follows. Total lipids were extracted according to the literature known in the art (J Invest Dermatol. 2010 October, 130(10):2472-80). Ceramides, sphingosine, and sphingosine-1-phosphate were derivatized with OPA (o-phthalaldehyde) reagent and quantified using a LC-MS/MS system equipped with a fluorescence detector (J Invest Dermatol. 2010 October, 130(10): 2472-80; Arch Pharm Res. 2009 December, 32(12):1795-801; Proc Natl Acad Sci USA. 2016 Mar. 8, 113(10): E1334-E1342). The amount of sphingolipids was expressed as "pmol/g of protein", and the quantification of proteins was performed according to a conventional BCA method.

Figure 12A:
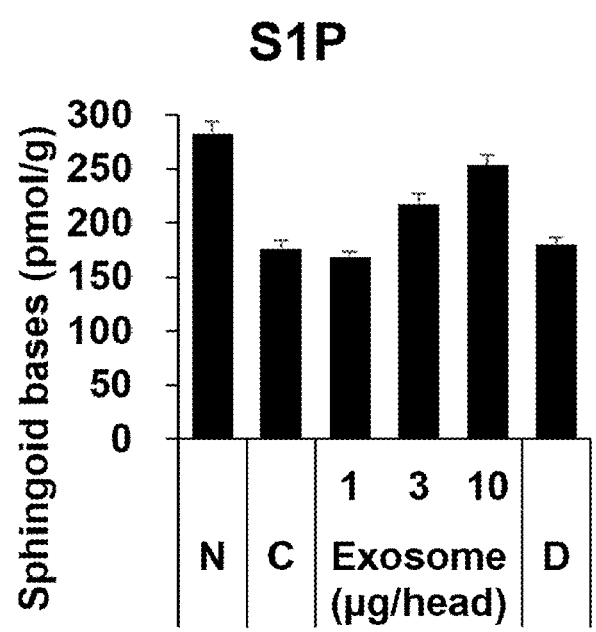
FIGS. 12A to 12B depict graphs showing that when mice, in which skin barrier damage was induced, were treated with the exosomes according to one embodiment of the present invention, the amount of sphingoid bases increased in the skin.
Figure 12B:
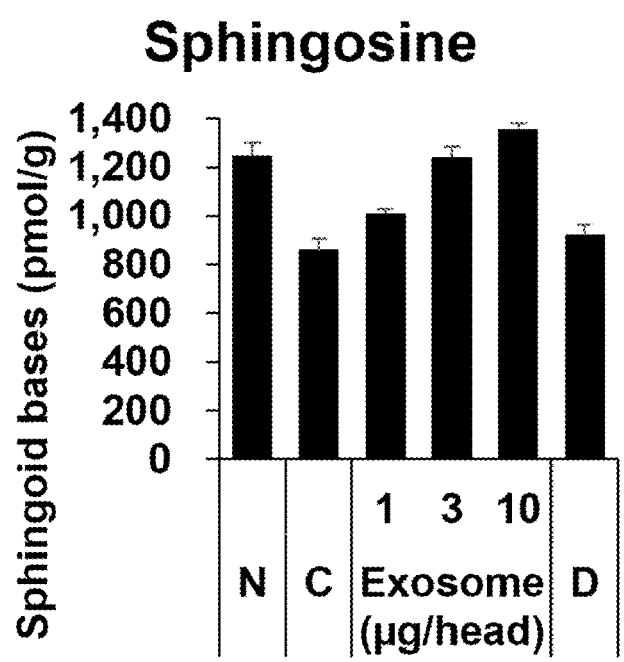

As shown in FIGS. 10A to 10G, it was confirmed that the amount of C16 ceramide, C18 ceramide, C20 ceramide, C22 ceramide, C24 ceramide, or C24:1 ceramide, and the amount of total ceramides in the skin tissues of test groups (3) to (5) treated with the exosomes according to one embodiment of the present invention, increased as compared with those in the disease control group. In addition, as shown in FIGS. 11A to 11F, it was confirmed that the amount of C16 dihydroceramide, C18 dihydroceramide, C22 dihydroceramide, C24 dihydroceramide, or C24:1 dihydroceramide, and the amount of total dihydroceramides in the skin tissues of test groups (3) to (5) treated with the exosomes according to one embodiment of the present invention, increased as compared with those in the disease control group. Further, as shown in FIGS. 12A and 12B, it was confirmed that the amounts of sphingosine-1-phosphate (S1P) and sphingosine in the skin tissues of test groups (3) to (5) treated with the exosomes according to one embodiment of the present invention, also increased as compared with those in the disease control group.

Meanwhile, the activity of sphingosine kinase 1 (SPHK1) was analyzed using LC-MS/MS as follows. Lysates of skin tissues in 20 mM Tris buffer (pH 7.4) containing 5 mM EDTA, 5 mM EGTA, 3 mM β-mercaptoethanol, 5% glycerol, protease inhibitors (Sigma-Aldrich) and phosphatase inhibitors (Roche), were incubated with 10 µL of 200 µM C17-sphingosine (SPHK1 substrate) (Avanti Polar Lipids). To evaluate the activity of SPHK1, 0.5% Triton X-100 was added to the assay buffer and incubated at 37° C. for 30 minutes. The enzymatic reaction was terminated by addition of $CHCl_3$:MeOH:HCl (8:4:3, v/v/v). C17-sphinganine-1-phosphate (100 pmol; Avanti Polar Lipids) was added as an internal standard. The organic phase separated by addition of $CHCl_3$ was dried under vacuum, and the dried product was re-dissolved in methanol, and then analyzed by LC-ESI-MS/MS (API 3200 Triple quadruple mass, AB/SCIEX). The activity of SPHK1 was expressed as "C17-S1P pmol/mg of protein/min", and the quantification of proteins was performed according to a conventional BCA method.

In addition, the activity of S1P lyase was analyzed using LC-MS/MS as follows. Lysates of skin tissues were incubated with 10 nmol of S1P (Avanti Polar Lipids) for 20 minutes. 100 pmol of (2E)-d5-hexadecenal (Avanti Polar Lipids) was added as an internal standard, and the reaction was terminated by lipid extraction. The total lipid extract was derivatized with 5-mM semicarbazide hydrochloride (Avanti Polar Lipids) in methanol containing 5% formic acid at 40° C. for 2 hours, and analyzed by LC-ESI-MS/MS. The activity of S1P lyase was expressed as "pentadecanal pmol/mg of protein/min", and the quantification of proteins was performed according to a conventional BCA method.

Figure 13:
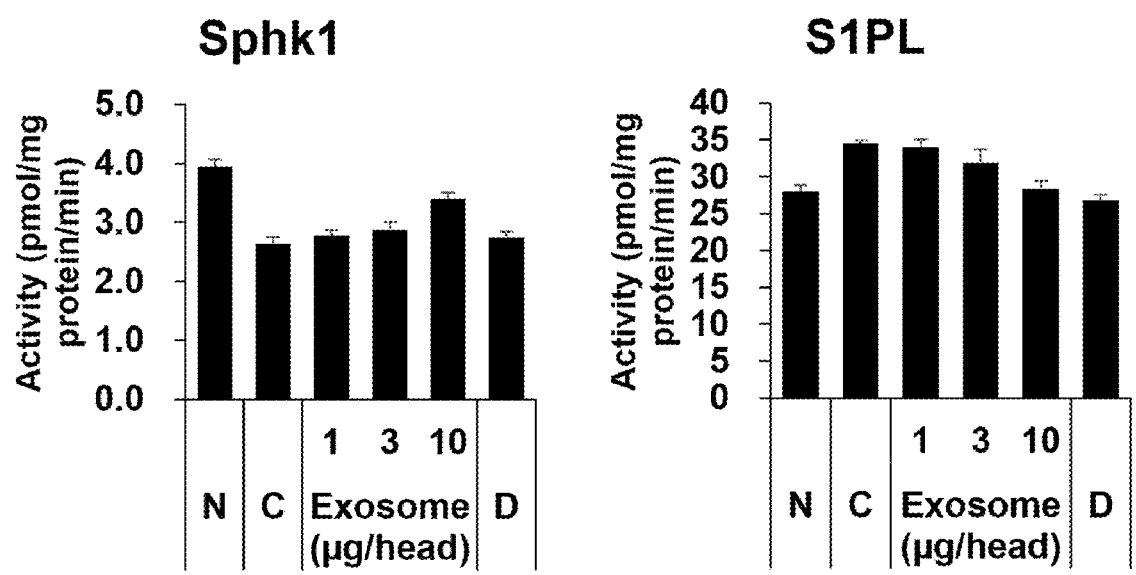
FIG. 13 depicts graphs showing that when mice, in which skin barrier damage was induced, were treated with the exosomes according to one embodiment of the present invention, the activity of SPHK1 increased in the skin and the activity of S1P lyase decreased in the skin.

As shown in FIG. 13, it was confirmed that in the skin tissues of test groups (3) to (5) treated with the exosomes according to one embodiment of the present invention, the activity of SPHK1 increased (28.79% increase) and the activity of S1P lyase decreased, as compared with those in the disease control group. Since SPHK1 is an enzyme that is involved in the synthesis of sphingolipids constituting the skin barrier, the increase in the activity thereof means the increased synthesis of ceramides and thus the strengthening of the skin barrier. In addition, since S1P lyase is an enzyme that interferes with the synthesis of sphingolipids by degrading sphingosine-1-phosphate, the decrease in the activity thereof means the decrease in the interference of the synthesis of ceramides and thus the strengthening of the skin barrier.

From the above-described results, it can be seen that the composition comprising, as an active ingredient, the exosomes according to one embodiment of the present invention, improves objective indicators related to the protection of skin barrier, the strengthening of skin barrier, and/or the improvement of skin barrier function, and shows, for example, an increase in production of ceramides, dihydroceramides and sphingoid bases, an increase in the activity of enzymes involved in the synthesis thereof, and a decrease in the activity of enzymes involved in the degradation thereof. Therefore, the composition comprising, as an active ingredient, the exosomes according to one embodiment of the present invention, is useful as a pharmaceutical composition, a skin external preparation and a cosmetic composition for strengthening skin barrier or improving skin barrier function.

Example 9: Comparison of the Ear Thickness and Spleen Size of Animal Model

The ear thicknesses of the mice of Example 7 were measured using a caliper, and the mice were euthanized. Then, for each test group, the back skin tissue was stained by an H&E staining method known in the art. The number of the mice was 8 for each test group (n=8).

Figure 14A:
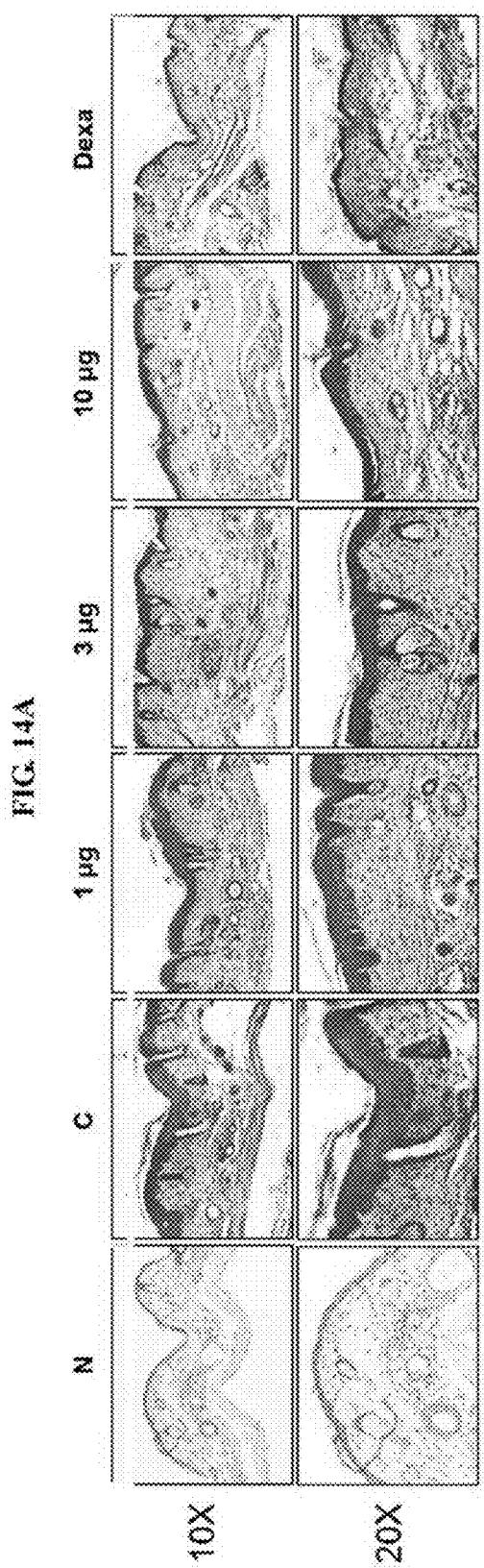
FIG. 14A shows tissue section images obtained after staining the back skin tissue of each group with H&E.
Figure 14B:
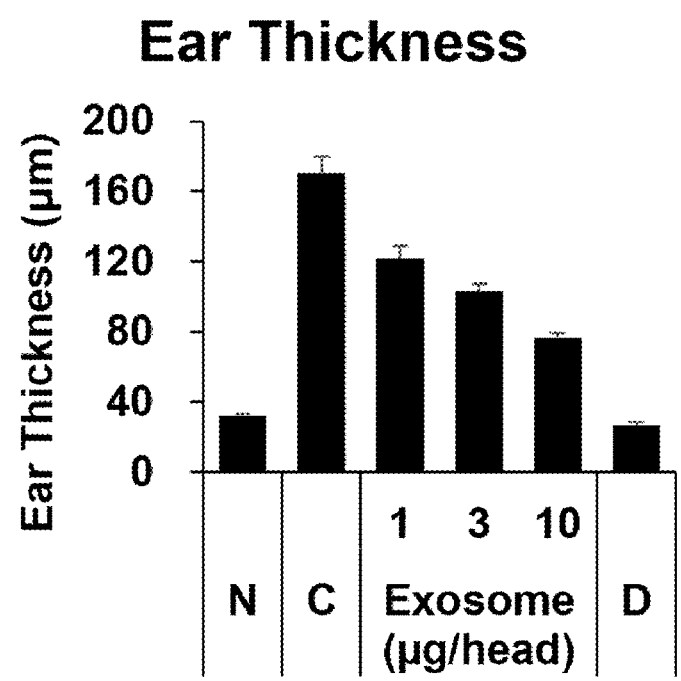
FIG. 14B is a graph which compares the ear thickness of each group with that of the other group.

FIG. 14A shows images of sections obtained after staining the skin tissues of the mice with H&E. FIG. 14B depicts a graph showing the ear thicknesses measured in each of test groups (2) to (6), in comparison with the ear thickness measured in normal group (1). It was confirmed that the ear thickness of each of test groups (3) to (5) treated with the exosomes according to one embodiment of the present invention decreased as compared with that of the disease control group in a manner of depending on the dose of the exosomes.

Meanwhile, the skin tissues of the euthanized mice were stained with toluidine blue, and then the infiltration of mast cells, a type of inflammatory cells, was measured. FIG. 15 shows images of sections obtained after staining the skin tissues of the mice with toluidine blue, and as shown therein, the filtration of mast cells in test group (5) treated with the exosomes according to one embodiment of the present invention (the group treated with a high dose of the exosomes) remarkably decreased. However, in the positive control group treated with dexamethasone, the infiltration of mast cells did not decrease.

The results show that the exosomes according to one embodiment of the present invention are able to inhibit or prevent the increase in epidermal thickness caused by inflammatory response and the infiltration of mast cells.

Figure 16:
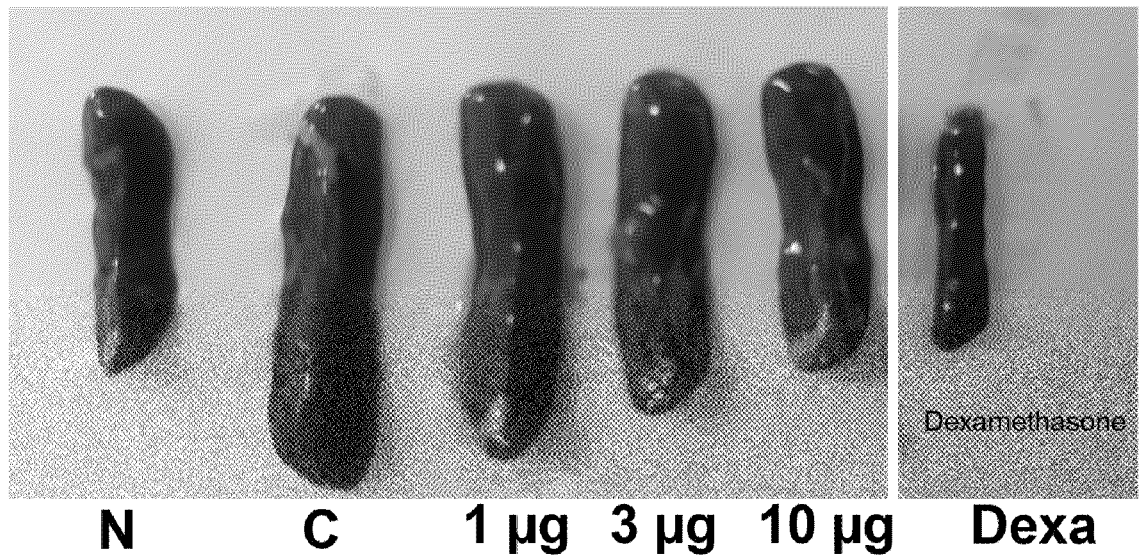
FIG. 16 is a photograph comparing the size of mouse spleen obtained from each group with that obtained from the other group.

In addition, it was confirmed that the spleen size of each of test groups (3) to (5) treated with the exosomes according to one embodiment of the present invention decreased as compared with that of the disease control group in a manner of depending on the dose of the exosomes (FIG. 16). This indicates that the exosomes according to one embodiment of the present invention inhibit or prevent the increase in spleen size that is closely associated with inflammatory response or immune response.

The test results show that the composition comprising the exosomes according to one embodiment of the present invention is able to prevent, suppress, alleviate or repair inflammatory response or impaired skin barrier function caused by the inflammatory response. Therefore, the composition for strengthening skin barrier or improving skin barrier function according to the present invention is useful for the protection of skin barrier, the strengthening of skin barrier, or the improvement of skin barrier function.

Example 10: Decrease in Cytokines Closely Associated with Skin Barrier Damage

The mice of Example 7 were euthanized and their skin samples were collected. Then, for each test group, the levels of thymic stromal lymphopoietin (TSLP), IL-4, IL-13 and the like in the skin tissue were measured by ELISA. The number of the mice used in the measurement was 8 for each test group (n=8). Each skin tissue sample was placed in 5 mL of RIPA buffer (containing 1× protease inhibitors) on ice and finely chopped, and then centrifuged at 2,000 rpm for 5 minutes at 4° C. to remove impurities. The quantification of proteins was performed using a BCA kit, and the protein concentration was adjusted to 100 µg/mL with RIPA buffer containing protease inhibitors. Then, 100 µL (10 µg of protein) was used in ELISA assay. The experiment was performed using a TSLP ELISA kit, an IL-4 ELISA kit and an IL-13 ELISA kit (purchased from ThermoFisher), and the absorbance was measured at 450 nm to quantify the levels of TSLP, IL-4 and IL-13 in the tissue.

Figure 20:
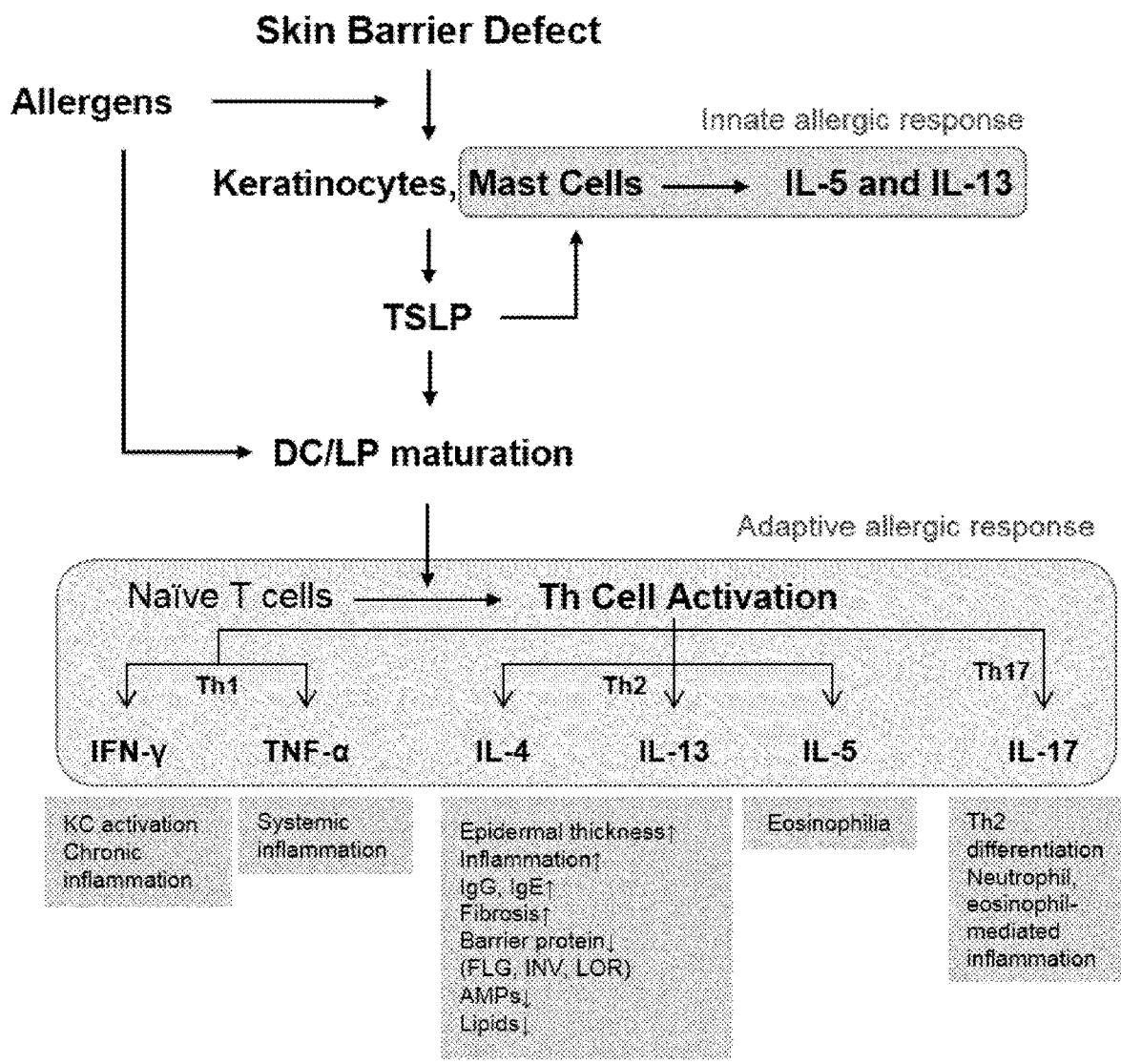
FIG. 20 is a diagram explaining that when the skin barrier is damaged, a vicious circle is repeated in which TSLP, IL-4, IL-13 and the like increase, and the increased Th2-type cytokines (IL-4 and IL-13) reduce the lipids and proteins that contribute to the skin barrier, thereby damaging the skin barrier.

Meanwhile, when the skin barrier is damaged, the secretion of TSLP from keratinocytes and mast cells is promoted, and the secreted TSLP is involved in the maturation of antigen-presenting cells (e.g., dendritic cells, Langerhans cells and the like). The matured antigen-presenting cells activate Th cells, and the activated Th cells increase Th2-type cytokines such as IL-4, IL-13 and the like. In this case, a vicious circle is repeated in which IL-4 and IL-13 further damage the skin barrier by reducing the lipids (e.g., ceramides) and proteins (e.g., filaggrin, involucrin and loricrin) that contribute to the skin barrier (see FIG. 20). Accordingly, it is considered that if a candidate substance that is likely to be involved in the restoration of skin barrier function reduces the expression and/or production of TSLP, IL-4 and/or IL-13, it can interrupt the aforesaid vicious circle, and thus contributes to the restoration of skin barrier function and the strengthening of skin barrier.

Figure 17:
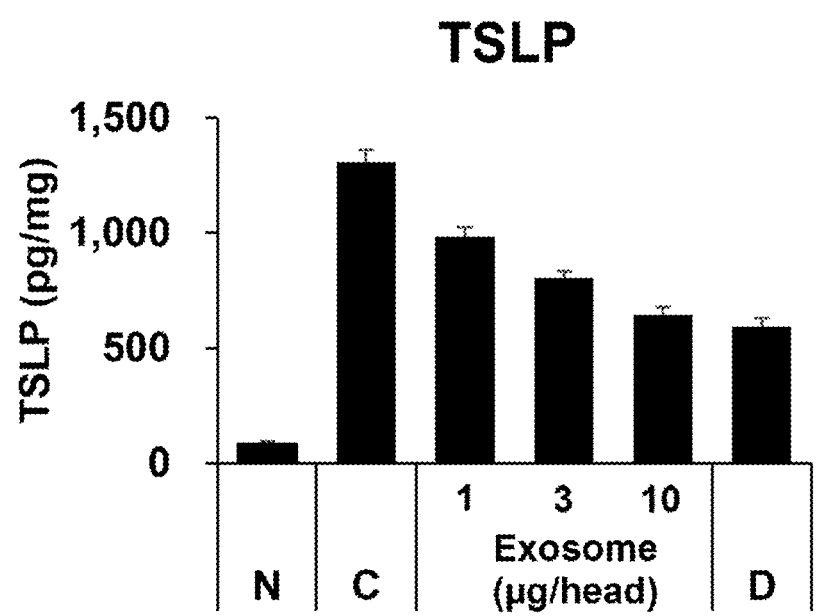
FIG. 17 is a graph showing the ELISA results indicating that when mice, in which skin barrier damage was induced, were treated with the exosomes according to one embodiment of the present invention, the level of TSLP decreased in the skin.
Figure 18:
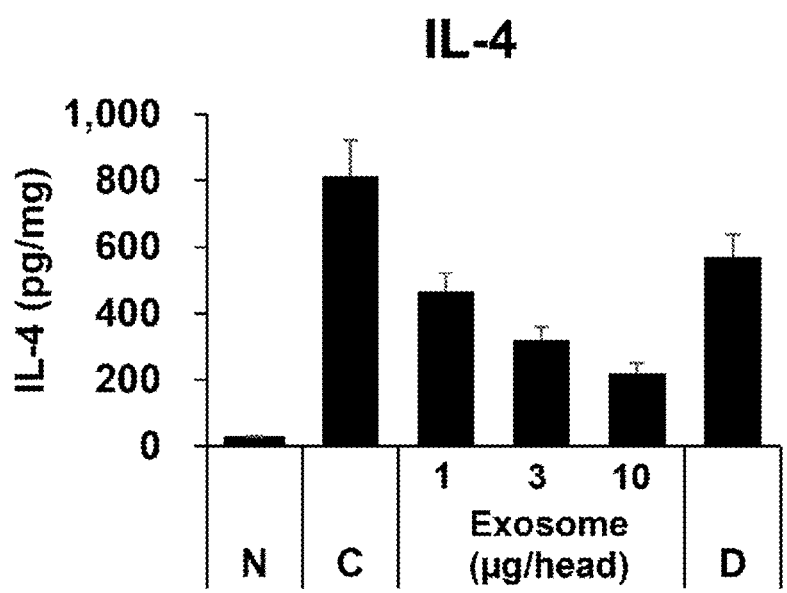
FIG. 18 is a graph showing the ELISA results indicating that when mice, in which skin barrier damage was induced, were treated with the exosomes according to one embodiment of the present invention, the level of IL-4 decreased in the skin.
Figure 19:
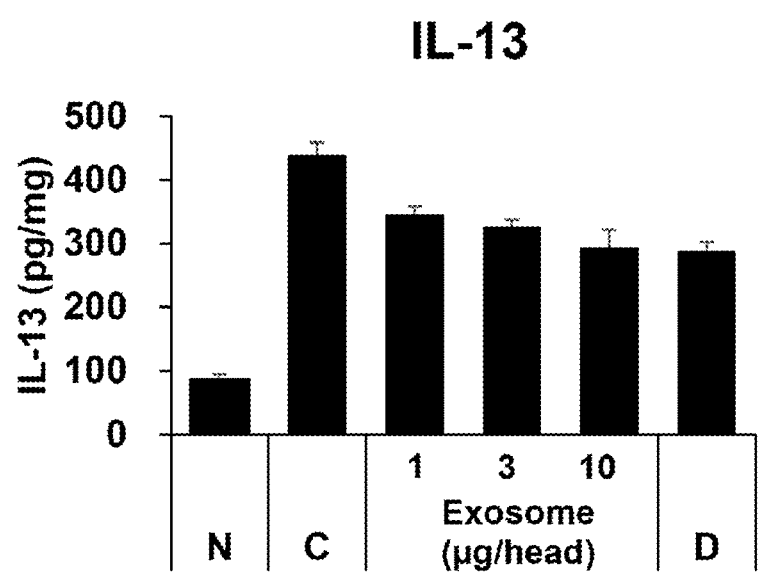
FIG. 19 is a graph showing the ELISA results indicating that when mice, in which skin barrier damage was induced, were treated with the exosomes according to one embodiment of the present invention, the level of IL-13 decreased in the skin.

As shown in FIGS. 17 to 19, it was confirmed that the levels of TSLP, IL-4 and IL-13 in the skin tissues of test groups (3) to (5) treated with the exosomes according to one embodiment of the present invention, remarkably decreased as compared with those in the disease control group. That is, it is considered that the exosomes according to one embodiment of the present invention remarkably reduces the level of TSLP in skin tissue, and thus inhibits the maturation of antigen-presenting cells, thereby suppressing Th2 activation. In addition, it is considered that the suppression of Th2 activation and the resulting decrease in Th2 cytokines of IL-4 and IL-13, by treatment with the exosomes according to one embodiment of the present invention, can lead to restore skin barrier function by interrupting the vicious circle in which the lipids and proteins contributing to the skin barrier decrease.

Example 11: Preparation of Cosmetic Composition Containing Exosomes of the Present Invention (Preparation of Lotion)

1704 µg/mL of the undiluted exosomes prepared in Example 2 above were diluted, mixed with and suspended in the components shown in Table 2 below, thereby preparing a cosmetic composition (lotion). The final cosmetic composition was prepared to contain the exosomes at a concentration of $2\times10^4$ particles/mL. The content of each component is shown in Table 2 below.

TABLE 2

Components and their contents of lotion

| Components | Contents (wt %) |
|---|---|
| Exosomes prepared in Example 2 | 1 |
| Glycerin | 7.375 |
| Caprylic/capric triglyceride | 6 |
| Cetyl ethylhexanoate | 5 |
| Propanediol | 5 |
| Phenyl trimethicone | 3.5 |
| Stearic acid | 3 |
| 1,2-hexanediol | 2 |
| Panthenol | 2 |
| Cetearyl olivate | 1.8 |
| Sorbitan olivate | 1.2 |
| Diisostearyl malate | 1 |
| Fructan | 1 |
| Ammonium acryloyldimethyl taurate/VP copolymer | 0.3 |
| Arachidyl alcohol | 0.25 |
| Behenyl alcohol | 0.15 |
| Arachidyl glucoside | 0.1 |
| Hydrogenated lecithin | 0.1 |
| Shea butter | 0.09 |
| Xanthan gum | 0.05 |
| Lavender oil | 0.02 |
| Bergamot oil | 0.02 |
| Ceramide NP | 0.02 |
| Orange peel oil | 0.02 |
| Phytospingosine | 0.015 |
| Palmitoyl tetrapeptide-7 | 0.01 |
| Palmitoyl tripeptide-1 | 0.01 |
| Purified water | Balance |

(Preparation of Cream)

1704 µg/mL of the undiluted exosomes prepared in Example 2 above were diluted, mixed with and suspended in the components shown in Table 3 below, thereby preparing a cosmetic composition (cream). The final cosmetic composition was prepared to contain the exosomes at a concentration of $2\times10^4$ particles/mL. The content of each component is shown in Table 3 below.

TABLE 3

Components and their contents of cream

| Components | Contents (wt %) |
|---|---|
| Exosomes prepared in Example 2 | 1 |
| Caprylic/capric triglyceride | 12 |
| Glycerin | 9.75 |
| Butylene glycol | 7 |
| Cetearyl alcohol | 3.5 |
| Hydrogenated vegetable oil | 3.5 |
| 1,2-hexanediol | 2 |
| Stearic acid | 2 |
| Phenyl trimethicone | 2 |
| Jojoba seed oil | 2 |
| Bees wax | 1.7 |
| Glyceryl stearate | 1.5 |
| Stearyl alcohol | 1.45 |
| Glyceryl stearate SE | 1 |
| Cetyl alcohol | 1 |
| Panthenol | 1 |
| Shea butter | 0.88 |
| Sorbitan sesquioleate | 0.5 |
| Polyglyceryl-2 stearate | 0.45 |
| Ammonium acryloyldimethyl taurate/VP copolymer | 0.3 |
| Hydrogenated lecithin | 0.1 |
| Bergamot oil | 0.04 |
| Ceramide NP | 0.04 |
| Phytospingosine | 0.03 |
| Coccinia Indica fruit extract | 0.0225 |
| Eclipta Prostrata extract | 0.0225 |
| Lavender oil | 0.02 |
| Orange peel oil | 0.02 |
| Copper tripeptide-1 | 0.01 |
| Palmitoyl tetrapeptide-7 | 0.01 |
| Palmitoyl tripeptide-1 | 0.01 |
| Calamine | 0.001 |
| Purified water | Balance |

(Preparation of Mask Pack)

1704 µg/mL of the undiluted exosomes prepared in Example 2 above were diluted, mixed with and suspended in the components shown in Table 4 below. Then, the obtained cosmetic composition was applied to or soaked in a mask pack. The exosomes were applied to or soaked in the mask pack at a concentration of $4\times10^3$ particles/mL. The content of each component is shown in Table 4 below.

TABLE 4

Components and their contents of mask pack

| Components | Contents (wt %) |
|---|---|
| Exosomes prepared in Example 2 | 0.1 |
| Glycerin | 3.070045 |
| Dipropylene glycol | 3.03 |
| Methyl propanediol | 2 |
| Caprylic/capric triglyceride | 1.500025 |
| Olive oil | 0.8 |
| 1,2-hexanediol | 0.7235 |
| Polysorbate 60 | 0.7 |
| Sorbitan stearate | 0.6475 |
| Arginine | 0.13 |
| Carbomer | 0.13 |
| Hydroxyl ethyl cellulose | 0.13 |
| Allantoin | 0.1 |
| Trehalose | 0.1 |
| Green tea extract | 0.07 |
| Butylene glycol | 0.07 |
| Ginger extract | 0.07 |
| Glycyrrhiza Glabra (Licorice) root extract | 0.07 |
| Coptis Chinensis root extract | 0.07 |
| Sucrose cocoate | 0.0525 |
| Ethylhexylglycerin | 0.05 |
| Dipotassium glycyrrhizate | 0.03 |

TABLE 4-continued

| Components and their contents of mask pack | |
|---|---|
| Components | Contents (wt %) |
| Disodium EDTA | 0.02 |
| Tocopheryl acetate | 0.02 |
| Panthenol | 0.02 |
| Ceramide NP | 0.000001 |
| Sodium hyaluronate | 0.01 |
| Xylitylglucoside | 0.004 |
| Anhydroxylitol | 0.0028 |
| Xylitol | 0.0012 |
| Glucose | 0.0004 |
| Hydrogenated lecithin | 0.000005 |
| Fragrance | 0.012 |
| Cholesterol | 0.000001 |
| Purified water | Balance |

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A method for strengthening skin barrier of multi-lamellar lipid layer of stratum corneum or improving skin barrier function of multi-lamellar lipid layer of stratum corneum, the method comprising:
administering a composition to a subject in need thereof, wherein the composition comprises exosomes derived from adipose-derived stem cells as an active ingredient, wherein the administering of the composition increases a production of at least one lipid selected from the group consisting of ceramides, dihydroceramides and sphingoid bases in skin of the subject.

2. The method of claim 1, wherein the administering of the composition increases the production of at least one lipid selected from the group consisting of C16 ceramide, C18 ceramide, C20 ceramide, C22 ceramide, C24 ceramide and C24:1 ceramide, and the total amount of ceramides in the skin.

3. The method of claim 1, wherein the administering of the composition increases the production of at least one lipid selected from the group consisting of C16 dihydroceramide, C18 dihydroceramide, C22 dihydroceramide, C24 dihydroceramide and C24:1 dihydroceramide, and the total amount of dihydroceramides in the skin.

4. The method of claim 1, wherein the administering of the composition increases the production of of sphingosine-1-phosphate and/or sphingosine in the skin.

5. The method of claim 1, wherein the administering of the composition increases the an activity of sphingosine kinase 1 in the skin, and decreases an activity of sphingosine-1-phosphate lyase in the skin.

6. The method of claim 1, wherein the administering of the composition decreases a production or expression of thymic stromal lymphopoietin, interleukin-4 and interleukin-13 in the skin.

7. The method of claim 1, wherein the composition is a pharmaceutical composition.

8. The method of claim 7, wherein the pharmaceutical composition is prepared as an injectable formulation.

9. The method of claim 1, wherein the subject is at least one animal selected from the group consisting of humans, dogs, cats, rodents, horses, cattle, monkeys and pigs.

10. A method for strengthening skin barrier of multi-lamellar lipid layer of stratum corneum or improving skin barrier function of multi-lamellar lipid layer of stratum corneum, the method comprising steps:
(a) (a1) applying a composition to a skin of a subject in need thereof, wherein the composition comprises exosomes derived from adipose-derived stem cells as an active ingredient; or (a2) contacting or attaching a patch, a mask pack or a mask sheet, which has the composition applied thereto or soaked therein, to the skin; or (a3) sequentially performing (a1) and (a2); and
(b) leaving the composition on the skin for a period of time sufficient to increase a production of at least one lipid selected from the group consisting of ceramides, dihydroceramides and sphingoid bases in the skin.

11. The method of claim 10, wherein the composition is a lotion or a cream in the step (a).

12. The method of claim 10, further comprising step (c) removing the patch, the mask pack, or the mask sheet from the skin after the step (b), and again applying the composition to the skin.

13. The method of claim 12, wherein the composition is a lotion or a cream in the step (c).

14. The method of claim 10, wherein the composition is used in at least one form selected from the group consisting of a cream, a tonic, an ointment, a suspension, an emulsion, a paste, a lotion, a gel, an oil, a spray, an aerosol, a mist, a foundation, a powder, and an oilpaper.

15. The method of claim 10, wherein the composition is a skin external preparation or a cosmetic composition.

16. The method of claim 10, wherein the subject is at least one animal selected from the group consisting of humans, dogs, cats, rodents, horses, cattle, monkeys and pigs.

17. A method for suppressing, alleviating, ameliorating or treating a skin disease caused by impaired skin barrier function of multi-lamellar lipid layer of stratum corneum, the method comprising:
administering a therapeutically effective amount of a pharmaceutical composition to a subject in need thereof, wherein the pharmaceutical composition comprises exosomes derived from adipose-derived stem cells as an active ingredient,
wherein the administering of the pharmaceutical composition increases a production of at least one lipid selected from the group consisting of ceramides, dihydroceramides and sphingoid bases in skin of the subject.

18. The method of claim 17, wherein the administering of the pharmaceutical composition increases the production of at least one lipid selected from the group consisting of C16 ceramide, C18 ceramide, C20 ceramide, C22 ceramide, C24 ceramide and C24:1 ceramide, and a total amount of ceramides in the skin.

19. The method of claim 17, wherein the administering of the pharmaceutical composition increases the production of at least one lipid selected from the group consisting of C16 dihydroceramide, C18 dihydroceramide, C22 dihydroceramide, C24 dihydroceramide and C24:1 dihydroceramide, and the total amount of dihydroceramides in the skin.

20. The method of claim 17, wherein the administering of the pharmaceutical composition increases the production of sphingosine-1-phosphate and/or sphingosine in the skin.

21. The method of claim 17, wherein the administering of the pharmaceutical composition increases an activity of sphingosine kinase 1 in the skin, and decreases an activity of sphingosine-1-phosphate lyase in the skin.

22. The method of claim 17, wherein the administering of the pharmaceutical composition decreases a production or expression of thymic stromal lymphopoietin, interleukin-4 and interleukin-13 in the skin.

23. The method of claim 17, wherein the pharmaceutical composition is prepared as in-an injectable formulation.

24. The method of claim 17, wherein the subject is at least one animal selected from the group consisting of humans, dogs, cats, rodents, horses, cattle, monkeys and pigs.

* * * * *